United States Patent [19]

Ichijima et al.

[11] Patent Number: 5,066,576

[45] Date of Patent: Nov. 19, 1991

[54] SILVER HALIDE COLOR PHOTOGRAPHIC MATERIAL

[75] Inventors: Seiji Ichijima; Naoki Saito; Keiji Mihayashi; Yoshio Ishii; Akira Ogawa, all of Kanagawa, Japan

[73] Assignee: Fuji Photo Film Co., Ltd., Kanagawa, Japan

[21] Appl. No.: 584,116

[22] Filed: Sep. 18, 1990

[30] Foreign Application Priority Data

Oct. 3, 1989 [JP] Japan .................................. 1-258512
Jul. 16, 1990 [JP] Japan .................................. 2-187798

[51] Int. Cl.$^5$ .............................................. G03C 7/36
[52] U.S. Cl. .................................... 430/558; 430/556; 430/557; 430/548
[58] Field of Search .................... 430/556, 557, 558 R, 430/558 A, 548

[56] References Cited

U.S. PATENT DOCUMENTS

| | | | |
|---|---|---|---|
| 2,214,483 | 9/1940 | Schneider et al. | 430/556 |
| 2,359,274 | 9/1944 | Wilson | 430/556 |
| 2,377,302 | 5/1945 | Wilson | 430/558 A |
| 2,380,809 | 6/1945 | Verkinderen et al. | 430/556 |
| 2,435,173 | 1/1948 | Bavley | 430/556 |
| 2,473,166 | 6/1949 | Mercky | 430/558 A |
| 2,668,112 | 2/1954 | de Cat et al. | 430/556 |
| 2,897,079 | 7/1959 | de Cat et al. | 430/558 A |
| 3,703,375 | 11/1972 | Groet et al. | 430/557 |
| 3,841,880 | 10/1974 | Kertel | 430/505 |
| 4,057,432 | 11/1977 | Fujiwhara et al. | 430/557 |
| 4,870,000 | 9/1989 | Bergthaller et al. | 430/557 |

OTHER PUBLICATIONS

*Chem. Abstr.* No. 89: 138.361n, vol. 89, 1978.
*Chem. Abstr.* No. 86:131064x, vol. 86, 1977.
*Chem. Abstr.* No. 88:113300h, vol. 88, 1978.

Primary Examiner—Richard L. Schilling
Attorney, Agent, or Firm—Birch, Stewart, Kolasch & Birch

[57] ABSTRACT

A silver halide color photographic material comprising a support having thereon at least one sensitive silver halide emulsion layer, wherein the emulsion layer contains a coupler represented by the following general formula (I)

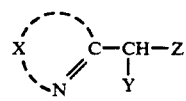

(I)

wherein X represents a non-metallic atomic group required for forming a heterocyclic ring together with a residue of the formula

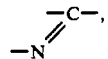

Y represents a group which is eliminated by coupling and has substantially no photographic effect and Z represents an electron attractive group (a substituent group having a value of at least 0.2 in terms of Hammett's σm substituent constant).

6 Claims, No Drawings

SILVER HALIDE COLOR PHOTOGRAPHIC MATERIAL

FIELD OF THE INVENTION

The present invention relates to a photographic coupler for forming an image. More particularly, the present invention relates to a color photographic material containing a photographic coupler capable of forming an image having excellent fastness to light.

BACKGROUND OF THE INVENTION

Color photographic materials are exposed and then developed and the oxidized aromatic primary amine developing agents react with the couplers to form images. In this system, the colors are reproduced by subtractive color photography and yellow, magenta and cyan dye images form in response to the blue, green and red complementary colors in order to reproduce these colors.

Acylacetanilide type couplers and malondianilide type couplers are widely known as conventional yellow couplers. Although conventional yellow couplers have been useful in the past, there is a need to further improve their characteristics. For instance, conventional yellow couplers produce images which have low fastness to light and hence, an improvement in fastness to light is required.

SUMMARY OF THE INVENTION

An object of the present invention is to provide a photographic coupler having an improved performance.

Another object of the present invention is to provide a color photographic material containing a photographic coupler capable of forming an image having excellent fastness to light.

The above-described objects have been achieved by providing a silver halide color photographic material comprising a support having thereon at least one light sensitive silver halide emulsion layer, wherein said emulsion layer contains a coupler represented by the following general formula (I)

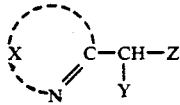
(I)

In formula (I), X represents a non-metallic atomic group required for forming a heterocyclic ring together with a residue of the formula

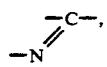

represents a coupling elimination group (a group which is eliminated by coupling) which has substantially no photographic effect and Z represents an electron attractive group (a substituent group having a value of at least 0.2 in terms of Hammett's σm substituent constant).

DETAILED DESCRIPTION OF THE INVENTION

The present invention will be illustrated in more detail below.

In formula (I), a heterocyclic ring represented by the formula

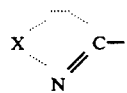

contains at least one nitrogen atom. All of the remaining ring-forming atoms may be carbon atoms, or some (e.g., one to two carbon atoms) of these carbon atoms may be replaced by one or more hetero-atoms such as a nitrogen atom, an oxygen atom or a sulfur atom. The thus-formed basic heterocyclic ring is a five-membered to seven-membered ring. The heterocyclic ring may have one or more substituent groups or other condensed rings. These condensed rings may be further substituted. Examples of the heterocyclic group include oxazol-2-yl, 1,2,4-triazol-3-yl (or -5-yl), benzoxazol-2-yl, 1,3,4-oxadiazol-2-yl, imidazol-2-yl, benzimidazol-2-yl, benzthiazol-2-yl, pyrimidin-2-yl (or -4-yl), 2-pyridyl, quinazolin-2-yl (or -4-yl), 2-imidazolin-2-yl, azocin-2-yl and 2H-azepin-7-yl. Examples of substituent groups for the heterocyclic groups include a saturated or unsaturated, straightchain, branched or cyclic substituted or unsubstituted alkyl group having 1 to 32 carbon atoms, preferably 1 to 20 carbon atoms (e.g., methyl, ethyl, butyl, t-butyl, cyclohexyl, dodecyl, hexadecyl, benzyl, 2-ethylhexyl, 3-dodecyloxypropyl), a substituted or unsubstituted aryl group having 6 to 20 carbon atoms (e.g., phenyl, 4-chlorophenyl, 2,4-dichlorophenyl), an alkoxycarbonyl group having 2 to 32 carbon atoms, preferably 2 to 20 carbon atoms (e.g., butoxycarbonyl, dodecyloxycarbonyl), an acylamino group having 2 to 32 carbon atoms, preferably 2 to 20 carbon atoms (e.g., acetamido, hexanamido, benzamido, 2-(2,4-di-t-amylphenoxy)butanamido, tetradecanamido), an alkoxy group having 1 to 32 carbon atoms, preferably 1 to 20 carbon atoms (e.g., methoxy, ethoxy, isopropoxy, 2-ethoxyethoxy), a sulfonamido group having 1 to 32 carbon atoms, preferably 1 to 20 carbon atoms (e.g., methanesulfonamido, octanesulfonamido, 4-methylbenzenesulfonamido), an alkylthio group having 1 to 32 carbon atoms, preferably 1 to 20 carbon atoms (e.g., methylthio, dodecylthio), a sulfonyl group having 1 to 32 carbon atoms, preferably 1 to 20 carbon atoms (e.g., benzenesulfonyl, methanesulfonyl), a heterocyclic group (e.g., those described above), a halogen atom (e.g., chlorine, fluorine), a nitro group, a carboxyl group, a cyano group, a carbamoyl group having 2 to 32 carbon atoms, preferably 2 to 20 carbon atoms (e.g., N,N-diethylcarbamoyl, N-methyl-N-dodecylcarbamoyl) and a sulfamoyl group having 1 to 32 carbon atoms, preferably 1 to 20 carbon atoms (e.g., N,N-diethylsulfamoyl, N-dodecylsulfamoyl).

As the group represented by Y in formula (I), conventional coupling elimination groups (groups which can be eliminated by coupling) can be used. In the present invention, Y is neither a useful photographic group nor a precursor thereof. Typical examples of the group Y include a substituted or unsubstituted aryloxy group having 6 to 10 carbon atoms (e.g., 4-(4-hydroxybenzenesulfonyl)phenoxy, 4-isopropoxycarbonylphenoxy, 2-butylsulfamoylphenoxy, 2-methylphenoxy) and a five-membered or six-membered nitrogen-containing unsaturated heterocyclic group (e.g., 1-pyrazolyl, 2-phenylcarbamoyl-1-imidazolyl, 3-chloro-1,2,4-triazol- 2-yl, 1-benzyl-5-ethoxy-2,4-dioxo-1,3-imidazolidin-3-yl, 5,5-dimethyl-2,4-dioxo-1,3-oxazolidin-3-yl, 1-benzyl-2-phenyl-3,5-dioxo-1,2,4-triazolidin-2-yl; excluding 1,2,3-triazoles).

Any of the substituent groups can be used as the group represented by Z in formula (I), so long as these groups have a value of at least 0.2 in terms of Hammett's σm substituent constant. Typical examples of 32 carbon atoms, preferably 2 to 20 carbon atoms (e.g., methoxycarbonyl, butoxycarbonyl, dodecyloxycarbonyl, 2-dodecanesulfonylethoxycarbonyl), a carbamoyl group having 2 to 32 carbon atoms, preferably 2 to 20 carbon atoms (e.g., dodecylcarbamoyl, phenylcarbamoyl, 2-chloro-5-dodecyloxycarbamoylphenylcarbamoyl, 2-methoxy-5-dodecyloxycarbonylphenylcarbamoyl, 2-tetradecyloxyphenylcarbamoyl), a sulfonyl group having 1 to 32 carbon atoms, preferably 1 to 20 carbon atoms (e.g., methanesulfonyl, hexadecanesulfonyl, benzenesulfonyl), a cyano group, a polyfluoroalkyl group having 1 to 8 carbon atoms, preferably 1 to 4 carbon atoms (e.g., trifluoromethyl), a sulfamoyl group having 1 to 32 carbon atoms, preferably 1 to 20 carbon atoms (e.g., dodecanesulfamoyl, phenylsulfamoyl) and an acyl group having 2 to 32 carbon atoms, preferably 2 to 20 carbon atoms (e.g., benzoyl, acetyl, 4-cyanobenzoyl).

Preferred compounds among the compounds of formula (I) are illustrated below.

Among the compounds of formula (I), the following compounds represented by general formula (II) or (III) are particularly preferred.

Formula (II):

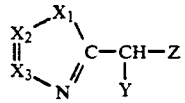

(II)

wherein Y and Z are as defined in formula (I), $X_1$ is an imino group, an oxygen atom or a sulfur atom, and $X_2$ and $X_3$ are each a methine group or a nitrogen atom.

The imino group represented by $X_1$ in formula (II) may be unsubstituted or substituted. Preferred examples of the substituent groups for the imino group include a substituted or unsubstituted aryl group having 6 to 10 carbon atoms (e.g., phenyl, 4-chlorophenyl, 2,4-dichlorophenyl) and a saturated or unsaturated straight-chain, branched or cyclic substituted or unsubstituted alkyl group having 1 to 32 carbon atoms, preferably 1 to 20 carbon atoms (e.g., methyl, ethyl, isopropyl, butyl, cyclohexyl, hexadecyl).

The methine group represented by $X_2$ and/or $X_3$ may be substituted. Examples of the substituent groups for the methine group include those already described above in the definition of the substituent groups for the heterocyclic rings formed by X in formula (I).

Formula (III):

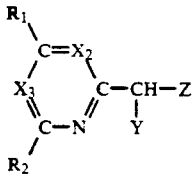

(III)

wherein Y and Z are as defined in formula (I), $X_2$ and $X_3$ are each a methine group or a nitrogen atom, and $R_1$ and $R_2$ are each a hydrogen atom or a group which can be substituted by an aromatic ring.

In formula (III), $X_2$ and $X_3$ are as defined in formula (II). When $R_1$ and $R_2$ are each a substituent group, examples of the substituent group include those described above in the definition of the substituent groups for the heterocyclic rings formed by X in formula (I).

Particularly preferred examples of the group represented by Y in formula (I) include an aryloxy group, a 2,4-di-oxo-1,3-imidazolidin-3-yl group, a 2,4-dioxo-1,3-oxazolidin-3-yl group, a 3,5-dioxo-1,2,4-triazolidin-4-yl group, a 1-pyrazolyl group and a 1-imidazolyl group. These groups may have one or more substituent groups. Examples of the substituent groups include those already described above in the definition of the substituent groups for the heterocyclic groups formed by X in formula (I).

Particularly preferred examples of the group represented by Z in formulas (I), (II) and (III) are a carbamoyl group, an alkoxycarbonyl group and a cyano group, with an arylcarbamoyl group being the most preferred.

It is preferred that the couplers represented by formulas (I), (II) and (III) are nondiffusing couplers. A nondiffusing coupler refers to a coupler into which one or more groups for increasing the molecular weight thereof are introduced so that the coupler is fixed to an emulsion layer containing said coupler. Usually, an alkyl group having 8 to 32 carbon atoms, preferably 10 to 20 carbon atoms (examples of the alkyl group including those already described above) or a substituted aryl group having 6 to 20 carbon atoms (examples of the aryl group including those already described above) is used as a nondiffusing group. These nondiffusing groups may be attached to any position of the molecule. The couplers may have one or more nondiffusing groups per molecule.

Among the couplers of formula (I), couplers capable of increasing the color density per unit weight are compounds represented by the following formulas (IV) and (V). The couplers of formula (IV) have two coupling groups per molecule and each coupling group enters a coupling reaction with an oxidant of a developing agent. As a result, the color density corresponding to the dye formed from the two couplers can be obtained by one coupler molecule. The couplers of formula (V) are characterized by having high molecular extinction coefficients of the formed azomethine dyes. Accordingly, the couplers of formulas (IV) and (V) produce a high color density per unit weight and the emulsion layers may be thinned or reduced in thickness so that the couplers can be advantageously used to improve sharpness.

Formula (IV):

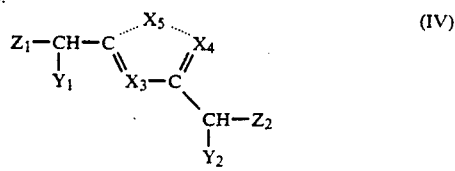

(IV)

wherein $Z_1$ and $Z_2$ each have the same meaning as Z in formula (I), $Y_1$ and $Y_2$ each have the same meaning as Y in formula (I), $X_3$ and $X_4$ are each a methine group or a nitrogen atom, $X_5$ is a non-metallic atomic group for forming a five-membered or six-membered ring together with

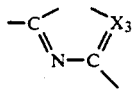

and at least one of $X_3$ and $X_4$ is a nitrogen atom.

Among the compounds represented by formulas (I) and (II), the compounds represented by the following general formula (V) are particularly preferred.

Formula (V):

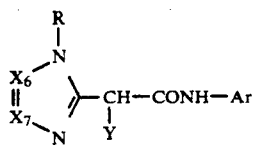

wherein Y is as defined in formula (I), $X_6$ and $X_7$ are each a methine group or a nitrogen atom, R is an alkyl group, an aryl group or a heterocyclic group, Ar is an aryl group, and $X_6$ and $X_7$ are not bonded to each other through their substituent groups to form a condensed ring.

The compounds represented by formula (V) are illustrated in more detail below.

The methine group represented by $X_6$ and $X_7$ may be substituted. Examples of the substituent groups include those described above in the definition of the substituent groups for the heterocyclic groups formed by X in formula (I).

Preferred examples of the alkyl group represented by R include saturated or unsaturated straight-chain, branched or cyclic substituted or unsubstituted alkyl groups having 1 to 32 carbon atoms, preferably 1 to 20 carbon atoms (e.g., methyl, ethyl, isopropyl, butyl, cyclohexyl, hexadecyl).

Preferred examples of the aryl group represented by R include substituted or unsubstituted aryl groups having 6 to 10 carbon atoms (e.g., phenyl, 4-chlorophenyl, 2,4-dichlorophenyl).

Preferred examples of the heterocyclic group represented by R include a saturated or unsaturated substituted or unsubstituted hetero-atom (nitrogen, sulfur or oxygen atom) containing three-membered to six-membered heterocyclic groups (e.g., 2-pyranyl, 2-pyrrolidinyl, 2-pyridinyl).

Examples of the aryl group represented by Ar include substituted or unsubstituted aryl groups having 6 to 10 carbon atoms. Examples of substituent groups for Ar include halogen (e.g., fluorine, chlorine), an alkoxycarbonyl group (having 2 to 30 carbon atoms, preferably 2 to 20 carbon atoms, e.g., methoxycarbonyl, dodecyloxycarbonyl, hexadecyloxycarbonyl), an acylamino group (having 2 to 30 carbon atoms, preferably 2 to 20 carbon atoms, e.g., acetamido, tetradecanamido, 2-(2,4-di-t-amylphenoxy)butanamido, benzamido), a sulfonamido group (having 1 to 30 carbon atoms, preferably 1 to 20 carbon atoms, e.g., methanesulfonamido, dodecanesulfonamido, hexadecanesulfonamido, benzenesulfonamido), a carbamoyl group (having 2 to 30 carbon atoms, preferably 2 to 20 carbon atoms, e.g., N-butylcarbamoyl, N,N-diethylcarbamoyl), a sulfamoyl group (having 1 to 30 carbon atoms, preferably 1 to 20 carbon atoms, e.g., N-butylsulfamoyl, N-dodecylsulfamoyl, N-hexadecylsulfamoyl, N-3-(2,4-di-t-amylphenoxy)butylsulfamoyl), an alkoxy group (having 1 to 30 carbon atoms, preferably 1 to 20 carbon atoms, e.g., methoxy, dodecyloxy), an alkyl group (the same as those set forth in the definition of R), an N-acylsulfamoyl group (having 2 to 30 carbon atoms, preferably 2 to 20 carbon atoms, e.g., N-propanoylsulfamoyl, N-tetradecanoylsulfamoyl), a sulfonyl group (having 1 to 30 carbon atoms, preferably 1 to 20 carbon atoms, e.g., methanesulfonyl, octanesulfonyl, dodecanesulfonyl), an alkoxycarbonyl group (having 1 to 30 carbon atoms, preferably 1 to 20 carbon atoms, e.g., methoxycarbonylamino, tetradecylcarbonylamino), a cyano group, a nitro group and a carboxyl group.

Preferred examples of the substituent groups for Ar are halogen, an alkoxycarbonyl group, an acylamino group, a sulfonamido group, an alkoxy group and a sulfamoyl group.

Examples of the couplers of the present invention include, but are not limited to, the following compounds.

Examples of the couplers represented by formulas (I) to (III)

| No. | | Y | Z |
|---|---|---|---|
| 1 | 2-methylbenzoxazole | N-(2-methoxy-2-methylpropanoyl)-oxazolidin-2-one | 4-chloro-3-(dodecyloxycarbonyl)phenylcarbamoyl |
| 2 | 2-methylbenzothiazole | 3-benzyl-5-ethoxy-oxazolidine-2,4-dione | 4-chloro-3-(hexadecylsulfonylamino)phenylcarbamoyl |
| 3 | 1-benzyl-2-methylbenzimidazole | N-(2-methoxy-2-methylpropanoyl)-oxazolidin-2-one | 4-chloro-3-(dodecyloxycarbonyl)phenylcarbamoyl |
| 4 | 5-methyl-1-phenyltetrazole | pyrazol-1-yl | 4-methoxy-3-(tetradecyloxycarbonyl)phenylcarbamoyl |

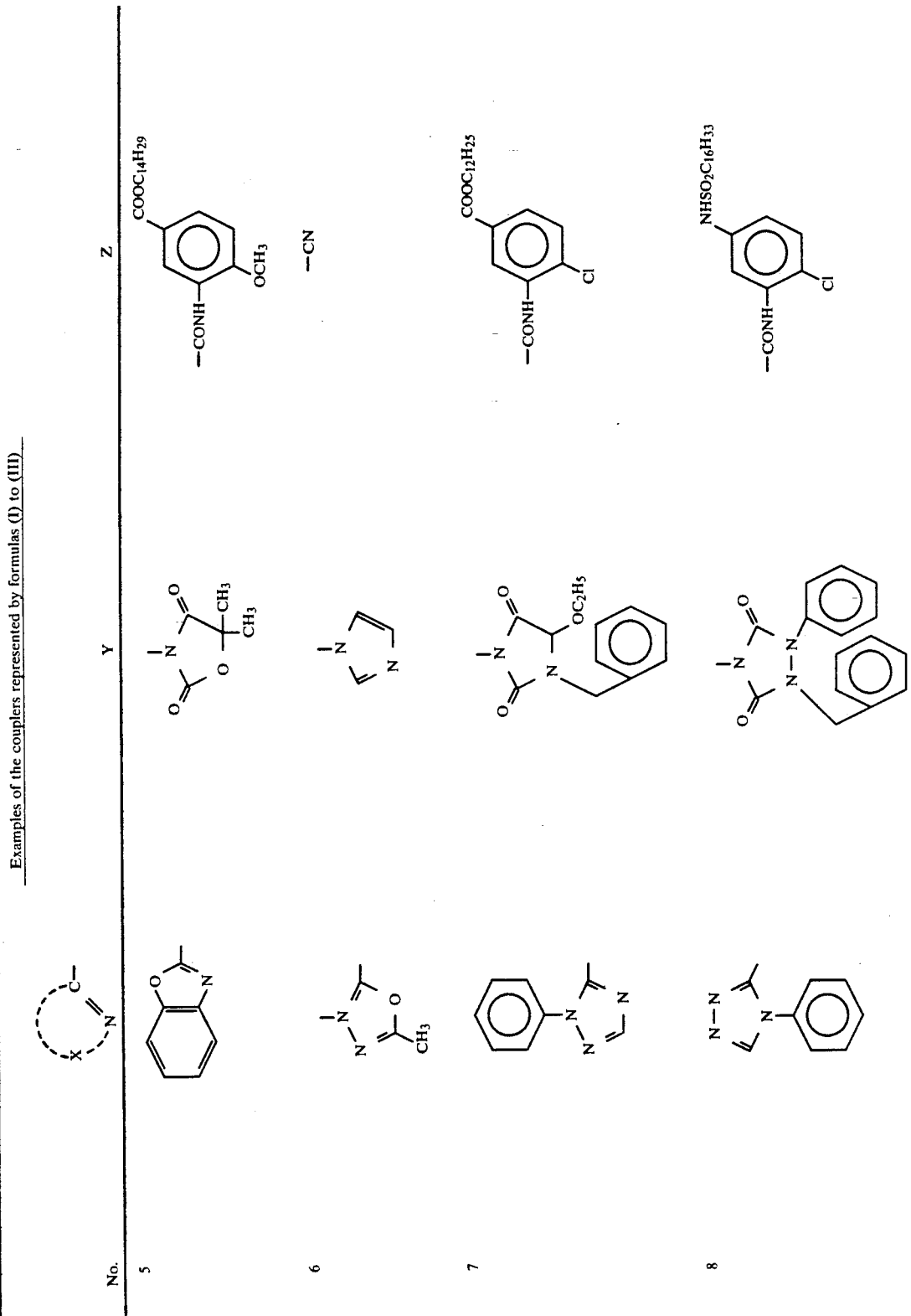

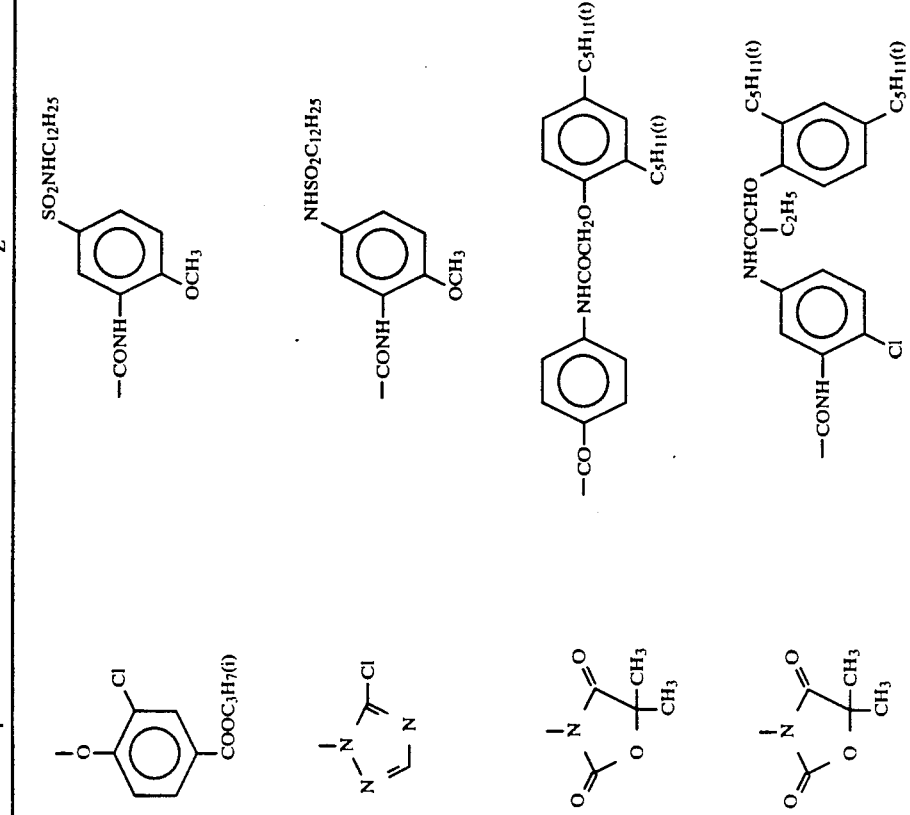

-continued

Examples of the couplers represented by formulas (I) to (III)

| No. | X‑‑‑C⟍N (ring) | Y | Z |
|---|---|---|---|
| 13 | quinazoline (benzo-fused with two N) | 3-benzyl-1-methylhydantoin-N-yl (phenyl-CH₂–N of imidazolidine-2,4-dione) | $-COOC_{16}H_{33}$ |
| 14 | 1-phenyl-1,2,4-triazole | 3-benzyl-1-methylhydantoin-N-yl | 2-($C_5H_{11}(t)$)-4-($C_5H_{11}(t)$)phenoxy-$(CH_2)_3$-CONH– attached to 4-chloro-3-(–CONH–)phenyl |
| 15 | quinazoline | 4-methoxyphenyl-SO₂-4-hydroxyphenyl ether | 2-($C_5H_{11}(t)$)-4-($C_5H_{11}(t)$)phenoxy-CH($C_2H_5$)-CONH– attached to 4-chloro-3-(–CONH–)phenyl |

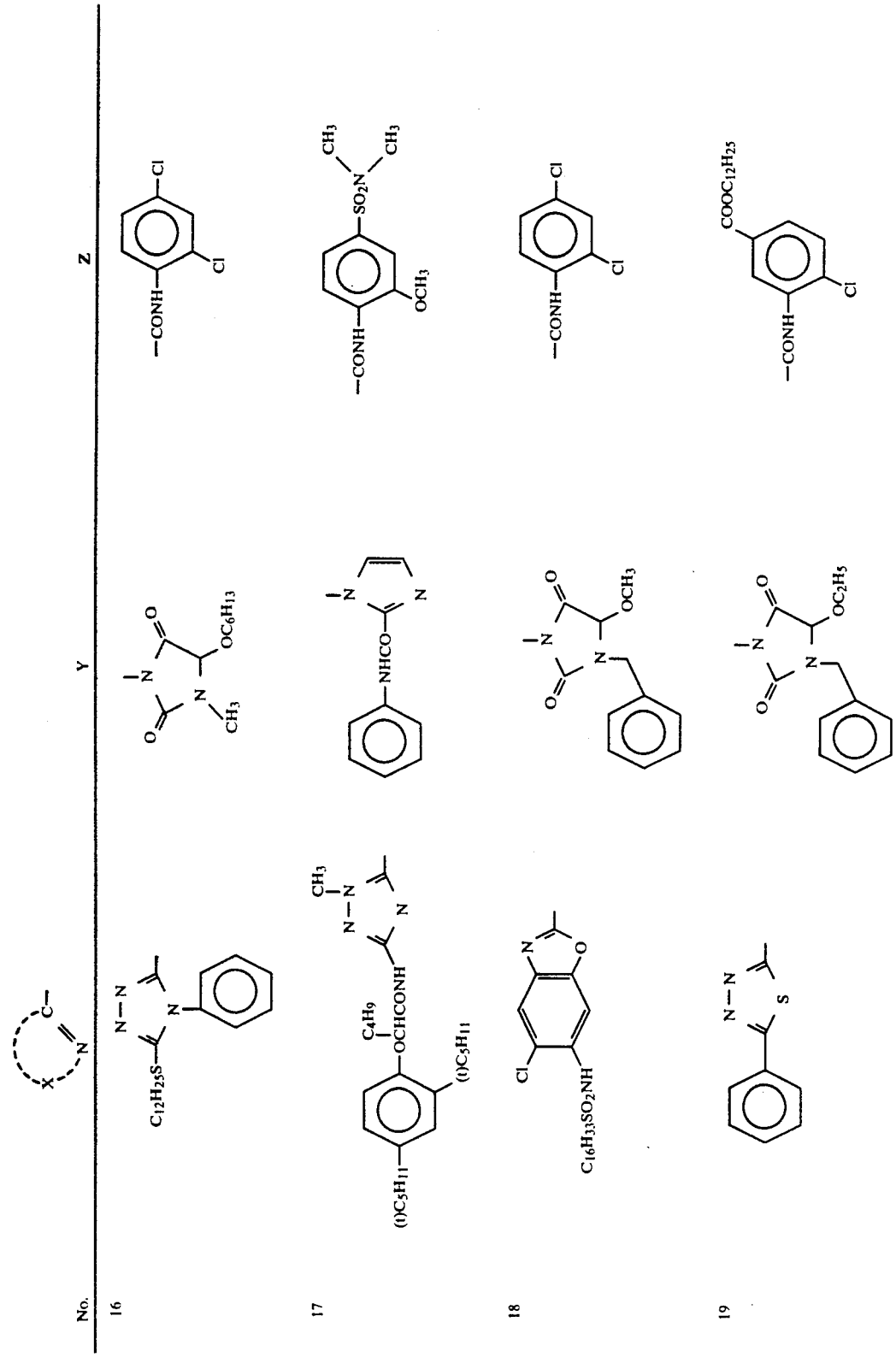

-continued

Examples of the couplers represented by formulas (I) to (III)

| No. | | Y | Z |
|---|---|---|---|
| 20 | pyrazole with NHCOC₁₃H₂₇, CH₃, and phenyl substituents | N-acyl oxazolidinone with gem-dimethyl | 4-chloro-3-(dodecyloxycarbonyl)phenyl carboxamide (−CONH−C₆H₃(Cl)(COOC₁₂H₂₅)) |
| 21 | 1,3-diphenyl pyrazole with methyl | 4-(4-methoxyphenylsulfonyl)phenol | 4-chloro-3-(hexadecylsulfonylamino)phenyl carboxamide (−CONH−C₆H₃(Cl)(NHSO₂C₁₆H₃₃)) |
| 22 | 1-methyl-2-methylbenzimidazole with C₁₆H₃₃OCO substituent | 2-methoxy-1,4-bis(methylsulfonyl)benzene | 2-chlorophenyl sulfonamide (−SO₂NH−C₆H₄Cl) |
| 23 | 1,3-diphenyl pyrazole with methyl | N-methyl-N'-(ethoxyacetyl) imide | 4-chloro-3-(hexadecylsulfonylamino)phenyl carboxamide (−CONH−C₆H₃(Cl)(NHSO₂C₁₆H₃₃)) |

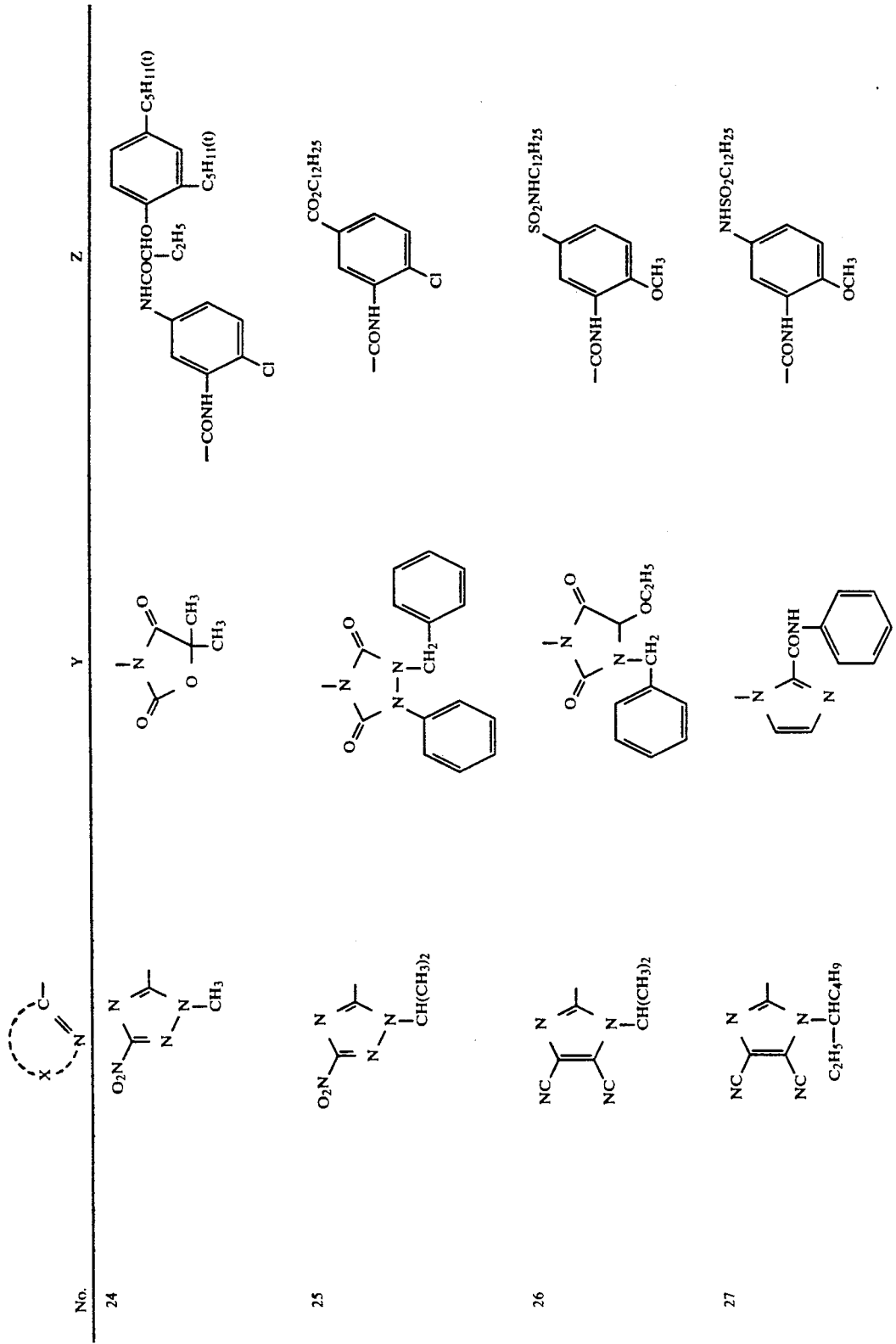

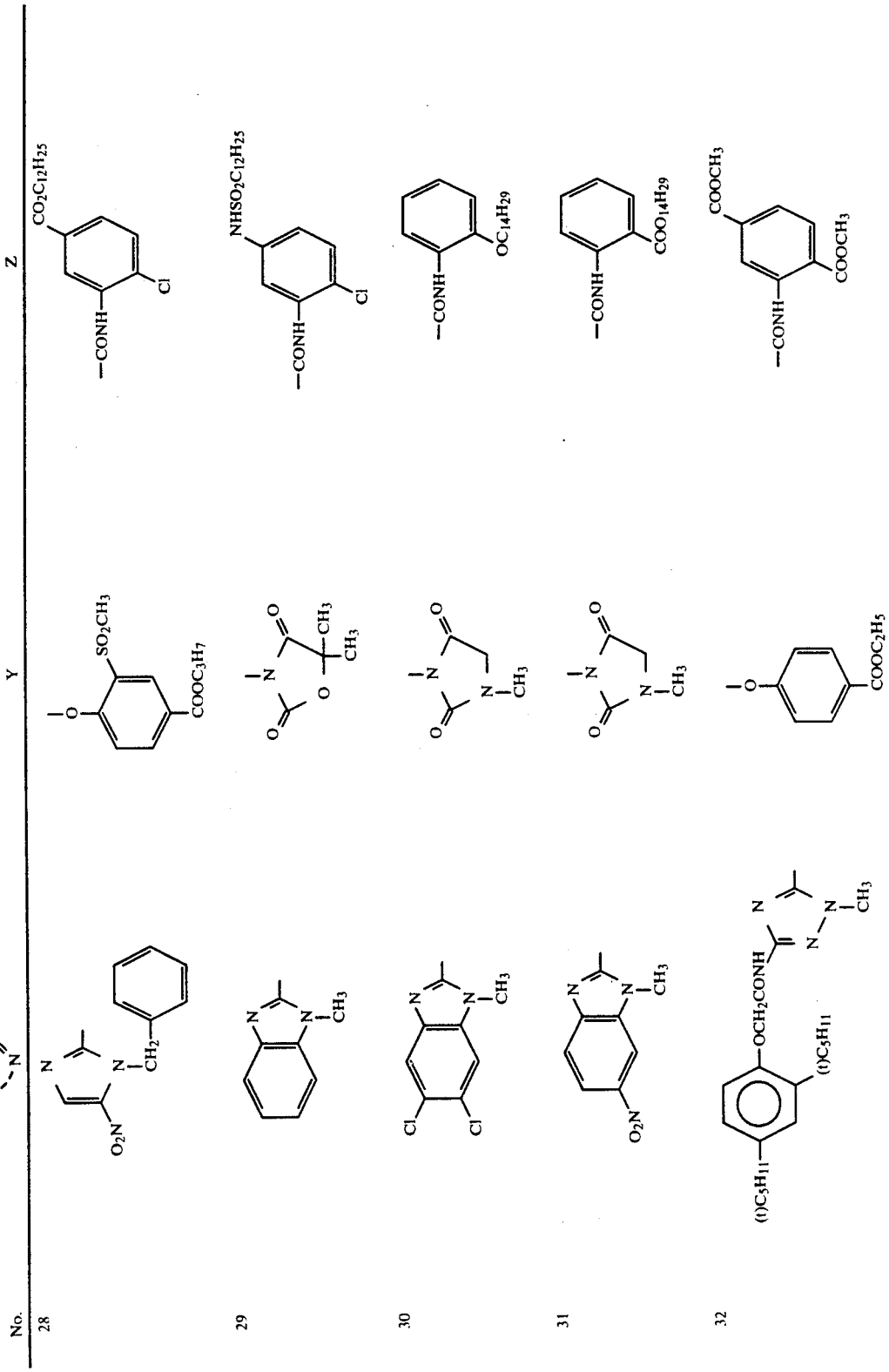

-continued

Examples of the couplers represented by formulas (I) to (III)

| No. | $\overset{|}{\underset{N}{\overset{C}{\underset{X}{\cdot}}}}$ | Y | Z |
|---|---|---|---|
| 33 | 2-methylthiazole | N-(5,5-dimethyl-2,4-dioxooxazolidin-3-yl) | —CONH—(4-chloro-3-{NHCO(CH$_2$)$_3$O-[2,4-di(t-C$_5$H$_{11}$)phenyl]}phenyl) |
| 34 | 2-methyl-4-methyloxazole | 1-phenyl-2-benzyl-3,5-dioxo-pyrazolidinyl | —CONH—(4-chloro-3-CO$_2$C$_{12}$H$_{25}$-substituted phenyl) |
| 35 | 2,5-dimethyl-4-methyloxazole | N-(α-methoxy-α-benzylacetyl) with phenyl | —CONH—(4-chloro-3-CO$_2$C$_{12}$H$_{25}$-substituted phenyl) |

Examples of the couplers of formula (IV):

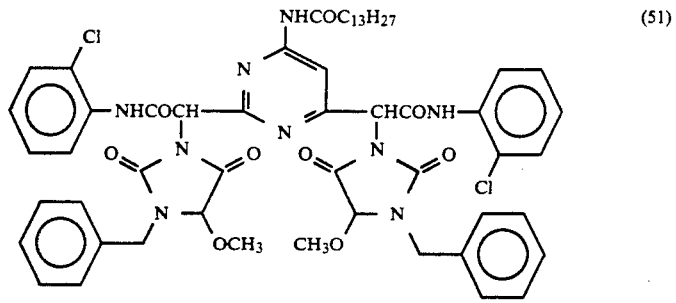

(51)

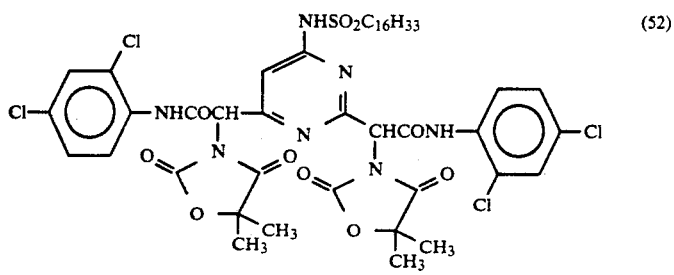

(52)

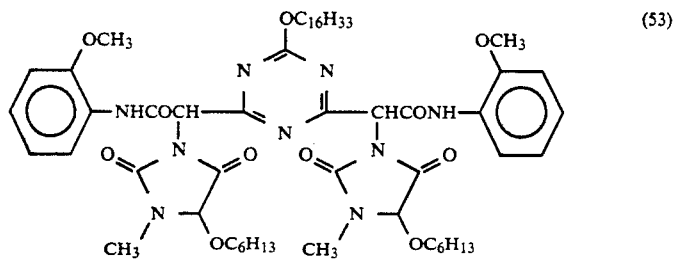

(53)

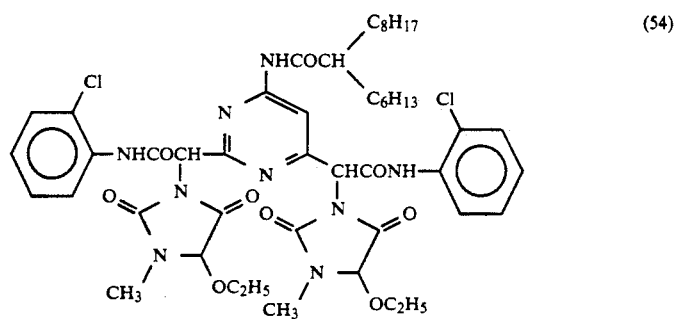

(54)

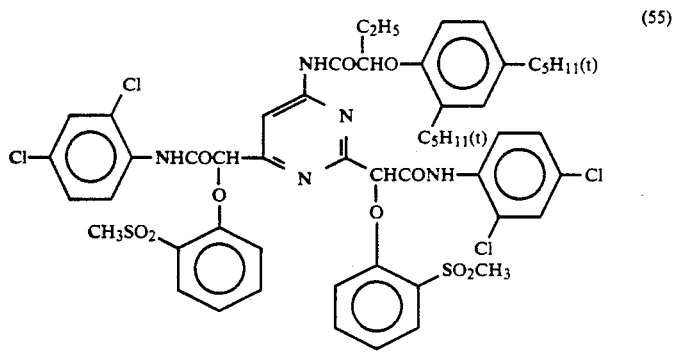

(55)

A method for synthesizing the compounds of the present invention is illustrated below.

Generally, the compounds of the present invention can be synthesized by any one of the conventional methods or a combination thereof. For example, the compounds of the present invention can be synthesized by the following synthesis route:

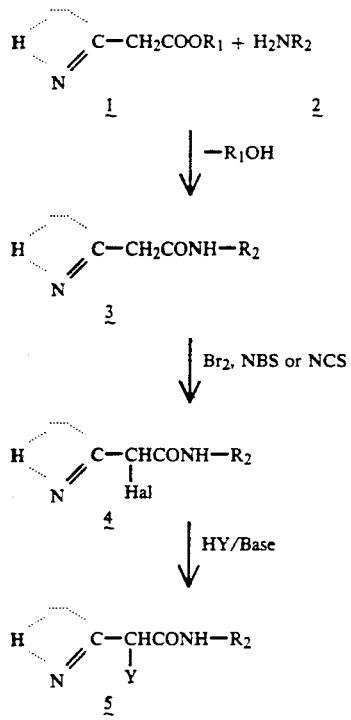

In the above scheme, a synthesis route where Z in formula (I) is a carbamoyl group is shown. In the above formulas in the synthesis route, X and Y are as defined in formula (I), $R_1$ is an alkyl group (e.g., methyl, ethyl) or an aryl group (e.g., phenyl), and $R_2$ has the same meaning as the case where Z is a carbamoyl group (that is, CONH—$R_2$ has the same meaning as Z). NBS is N-bromosuccinimide, NCS is N-chlorosuccinimide and Hal is bromine or chlorine atom. In the reaction of 4→5, a base is generally used. Examples of the base include triethylamine, DBU, guanidine, potassium hydroxide, sodium hydroxide and t-butoxy-potassium.

Methods for synthesizing the compound 1 and/or the compound 5 and methods for synthesizing the compounds of formula (1) are described in the following literature references.

| J. Heterocyclic Chem., | 20, 73 (1983); |
| | 24, 697 (1987); |
| " | 18, 1397 (1981); |
| " | 22, 1487 (1985); |
| Chem. Ber., | 102, 2530 (1969); |
| " | 97, 1134 (1964); |

J. Org. Chem., 40, 252 (1975);
Synthesis, 28 (1974);
Can. J. Chem., 46, 2255;
Compt. Rend., 261, 5520(1965);
Bull. Chem. Soc. Japan, 46, 3600 (1973);
U.S. Pat. No. 4,562,186; JP-B-47-47029 (the term "JP-B" as used herein means an "examined Japanese patent publication"); JP-A-52-82423 (the term "JP-A" as used herein means an "unexamined published Japanese patent application"); JP-A-51-104825.

Typical synthesis examples are illustrated below. Other compounds can be obtained in a similar manner to that described below.

Synthesis Example 1

The compound was synthesized by the following synthesis route:

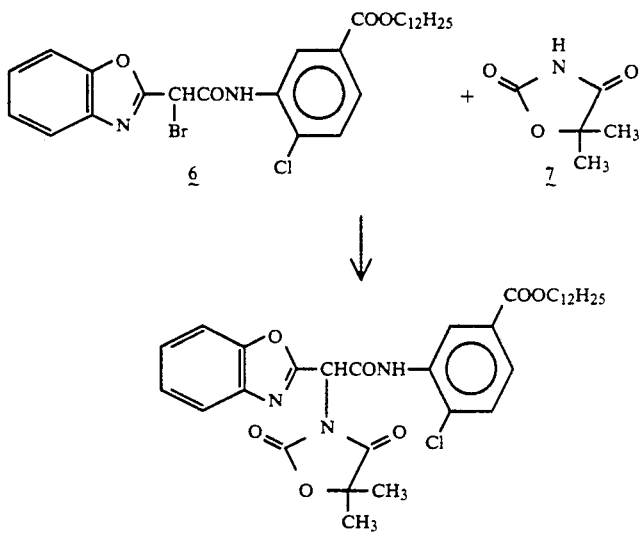

Compound (1)

24.4 g of compound 7 and 18.4 g of triethylamine were dissolved in 500 ml of N,N-dimethylformamide. 50 ml of chloroform solution containing 36.3 g of compound 6 dissolved therein was added dropwise thereto. The mixture was stirred at room temperature for 2 hours. One liter of ethyl acetate was added thereto and the mixture was washed with water by using a separating funnel. After the mixture was neutralized with dilute hydrochloric acid, the mixture was washed with water until the mixture became neutral to separate an oily layer. The solvents were distilled off and the product was separated from the residue (oil) and purified by means of silica gel column chromatography, eluting with ethyl acetate/hexane (1/6). 20.6 g of compound (1) was obtained.

Synthesis Example 2

Synthesis of compound (10)

The compound was synthesized by the following synthesis route:

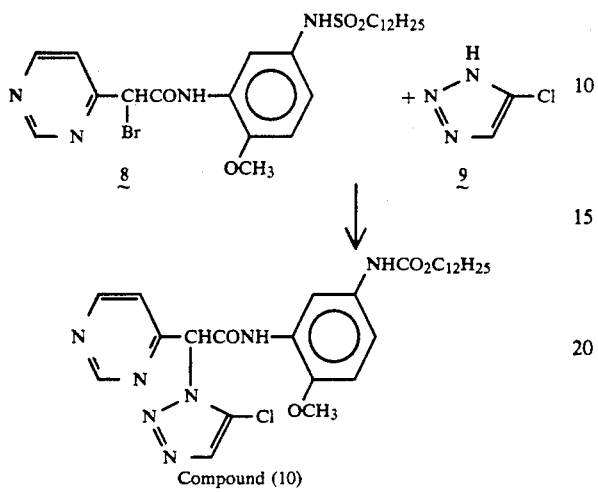

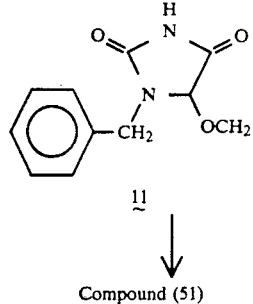

In the same way as in Synthesis Example 1, 18.4 g of compound (10) was obtained by using 34.2 g of compound 8, 12.4 g of compound 9 and 12.2 g of triethylamine.

Synthesis Example 3

Synthesis of compound (51)

The compound was synthesized by the following synthesis route:

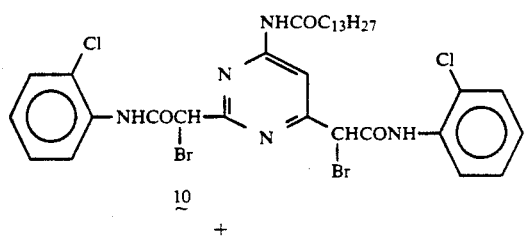

In the same way as in Synthesis Example 1, 15.4 g of compound (51) was obtained by using 24.0 g of compound 10, 26.4 g of compound 11 and 24.3 g of triethylamine.

Synthesis Example 4

Synthesis of compound (24)

The compound was synthesized by the following synthesis route:

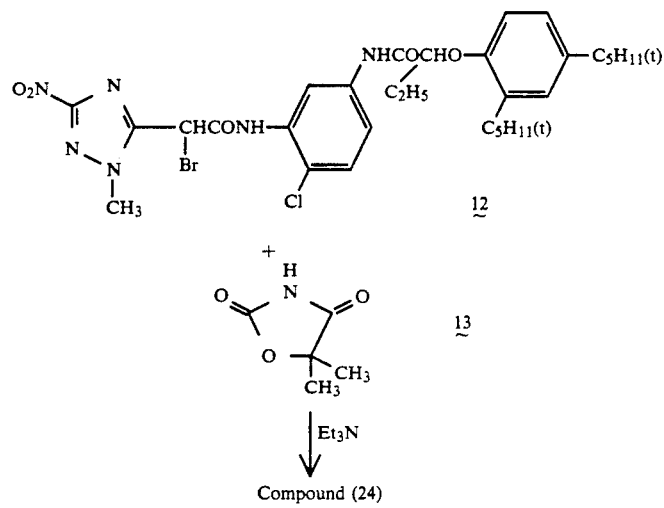

5.2 g of compound 13 and 4 g of triethylamine were dissolved in 50 ml of N,N-dimethylformamide. To the resulting solution, there was added dropwise 50 ml of chloroform solution containing 13.8 g of compound 12 dissolved therein at room temperature. After the mixture reacted for 2 hours, 200 ml of ethyl acetate was added to the reaction mixture and the resulting mixture was washed with water using a separating funnel. The oily layer was recovered, neutralized with dilute hydrochloric acid and washed with water until the layer became neutral. After the oily layer was dried over anhydrous sodium sulfate, the solvents were distilled off under reduced pressure. Ethyl acetate and hexane were added to the residue and the precipitated crystal was recovered by filtration to obtain 5.4 g of compound (24).

The compounds of the present invention can be applied to multi-layer color photographic materials comprising a support having thereon multiple emulsion layers having at least three different spectral sensitivity to improve fastness to light. The multilayer color photographic material usually comprises a support having thereon at least one red-sensitive emulsion layer, at least one green-sensitive layer and at least one blue-sensitive layer. The order of these layers may be arbitrarily chosen as the occasion demands. The compounds of the present invention may be added to any of the color-sensitive layers, but the compounds are usually used in the blue-sensitive layer or in adjacent layers (interlayers) thereto. If desired, the compounds of the present invention may be used in a high-sensitivity layer, a medium-sensitivity layer or a low-sensitivity layer.

The amounts of the compounds of the present invention to be used vary depending on the structures of the compounds, but the compounds are used in an amount of preferably $1 \times 10^{-6}$ to 1.0 mol, more preferably $1 \times 10^{-4}$ to 0.5 mol per mol of silver contained in the same layer or adjacent layer.

The amount of the high-boiling organic solvents to be added to the layer containing the yellow coupler of the present invention are in a ratio of the solvent to the total amount of yellow couplers contained in the layer containing the yellow coupler of the present invention of preferably not higher than 2, particularly preferably not higher than 0.7 by weight.

The yellow couplers of the present invention may be used together with conventional yellow couplers, but it is preferred that the amount of the yellow coupler of the present invention accounts for at least 50% of the amount of the entire yellow couplers. When the amount of the yellow couplers of the present invention are greater than 50%, the effect of the present invention is remarkable.

The photographic material of the present invention may comprise a support having thereon at least one layer of a blue-sensitive silver halide emulsion layer, a green-sensitive silver halide emulsion layer and a red-sensitive silver halide emulsion layer. There are no particular limitations with regard to the number of silver halide emulsion layers, the number of nonsensitive layers and the order of these layers. In a typical embodiment, the photographic material is a silver halide photographic material having at least one sensitive layer comprising a plurality of silver halide emulsion layers having substantially the same color sensitivity, but different light sensitivity, said sensitive layer being a unit sensitive layer having color sensitivity to any one of blue light, green light and red light. In a multi-layer silver halide color photographic material, unit sensitive layers are generally arranged in order of red-sensitive layer, green-sensitive layer and blue-sensitive layer from the side of the support. However, the arrangement may be in the reverse order to that described above or the arrangement may be in such an order that a different sensitive layer is interposed between the same color sensitive layers according to the intended purposes.

If desired, non-sensitive layers such as various interlayers may be provided between silver halide sensitive layers or on the uppermost layer or on the lowermost layer.

The interlayers may contain couplers and DIR compounds described in JP-A-61-43748, JP-A-59-113438, JP-A-59-113440; JP-A-61-20037 and JP-A-61-20038 and may contain color-mixing inhibitors conventionally.

A plurality of silver halide emulsion layers constituting each unit sensitive layer preferably comprises two layers composed of a high-sensitivity emulsion layer and a low-sensitivity emulsion layer as described in West German Patent 1,121,470 or U.K. Patent 923,045. It is usually preferred that the light sensitivity becomes lower toward the support. A non-sensitive layer may be provided between the silver halide emulsion layers. Alternatively, the low sensitivity emulsion layer may be provided on the farthest side of the support and the high-sensitivity emulsion layer may be provided on the side nearer the support as described in JP-A-57-112751, JP A-62-200350, JP-A-62-206541 and JP-A-62-206543.

For examples, the layers are arranged in order of low-sensitivity blue-sensitive layer (BL)/high-sensitivity blue-sensitive layer (BH)/high-sensitivity green-sensitive layer (GH)/low-sensitivity green-sensitive layer (GL)/high-sensitivity red-sensitive layer (RH)/low-sensitivity red-sensitive layer (RL), or in order of BH/BL/GL/GH/RH/RL or in order of BH/BL/GH/GL/RL/RH from the farthest side of the support.

The layers may be arranged in order of blue-sensitive layer/GH/RH/GL/RL from the farthest side of the support as described in JP-B-55-34932. Further, the layers may be arranged in order of blue-sensitive layer/GL/RL/GH/RH from the farthest side of the support as described in JP-A-56-25738 and JP-A-62-63936.

The sensitive layer may be composed of three layers having different light sensitivities in such an arrangement that the upper layer is composed of a silver halide emulsion layer having the highest light sensitivity. The medium layer is composed of a silver halide emulsion layer having a light sensitivity lower than that of the upper layer. The lower layer is composed of a silver halide emulsion layer having a light sensitivity lower than that of the medium layer. Thus, the light sensitivity becomes lower toward the support as described in JP-B-49-15495. Even when the sensitive layer is composed of three layers having different light sensitivities as mentioned above, these layers may be arranged in the order of medium-sensitivity emulsion layer/high-sensitivity emulsion layer/low-sensitivity emulsion layer in the same color-sensitive layer from the farthest side of the support as described in JP-A-59-202464.

Further, these layers may be arranged in order of high-sensitivity emulsion layer/low sensitivity emulsion layer/medium-sensitivity emulsion layer or in order of low-sensitivity emulsion layer/medium-sensitivity emulsion layer/high-sensitivity emulsion layer.

When four or more layers are used, various arrangements can also be used as described above.

It is preferred that donor layers (CL) having a multilayer effect and a different spectral sensitivity distribution from that of the principal sensitive layers (e.g., BL, GL, RL, etc.) are arranged so as to be adjacent to or near the principal sensitive layers to improve color reproducibility, said donor layers being described in U.S. Pat. Nos. 4,663,271, 4,705,744 and 4,707,436, JP-A-62-160448 and 63-89580.

Various layer structures and arrangements can be chosen according to the purposes of the photographic materials as mentioned above.

Preferred silver halides to be used in the photographic emulsion layers of the photographic materials of the present invention are silver iodobromide, silver iodochloride and silver iodochlorobromide, each having a silver iodide content of not higher than about 30 mol%. Particularly preferred silver halides are silver iodobromide and silver iodochlorobromide, each having a silver iodide content of from about 2 to about 25 mol%.

Silver halide grains in the photographic emulsions may have a regular crystal form such as a cube, octahedron or tetradecahedron, an irregular crystal form such as a sphere or tabular form, a defective crystal form such as a crystal form having a twinning plane or a composite form thereof.

The size of the silver halide may be in the range of from fine grains having a grain size of not larger than about 2 μm to large-size grains having a diameter (in terms of projected area) of about 10 μm. Any of the polydisperse emulsion and monodisperse emulsion can be used.

The silver halide photographic emulsions of the present invention can be prepared according to the methods described in *Research Disclosure* (RD) No. 17643 (December 1978), pages 22 to 23, "I. Emulsion preparation and types"; P. Glafkides, *Chemie et Rhisique Photographique*, Paul Montel, 1967; G. F. Duffin, *Photographic Emulsion Chemistry* (Focal Press, 1966); and V. L. Zelikman et al., *Making and Coating Photographic Emulsion*, Focal Press, 1964.

Monodisperse emulsions described in U.S. Pat. Nos. 3,574,628 and 3,655,394 and U.K. Patent 1,413,748 are also preferred.

Tabular grains having an aspect ratio of not lower than about 5 can also be used in the present invention. The tabular grains can be easily prepared by methods described in Gutoff, *Photographic Science and Engineering*, Vol. 14, pp. 248 to 257 (1970), U.S. Pat. Nos. 4,434,226, 4,414,230, 4,433,048 and 4,439,520 and U.K. Patent 2,112,157.

The crystal structure may be uniform or different with respect to the halogen composition between the interior of the crystal and the exterior surface thereof, or the crystal structure may have a laminar structure. Silver halide having a different halogen composition may be bonded to grains by epitaxial growth. A compound such as silver rhodanide or lead oxide other than silver halide may be bonded to the grains.

Mixtures of grains having various crystal forms may be used.

Usually, silver halide emulsions are subjected to physical ripening and chemical ripening spectral sensitization prior to being used. Additives used in these steps are described in *Research Disclosure* No. 17643 and ibid. No. 18716 and are summarized in the following Table.

Conventional photographic additives which can be used in the present invention are described in the above-described two Research Disclosures and are also shown in the following Table.

| | Type of additive | RD 17643 | RD 18716 |
|---|---|---|---|
| 1. | Chemical sensitizing agent | page 23 | page 648 (right column) |
| 2 | Sensitivity increaser | | page 648 (right column) |
| 3. | Spectral sensitizing agent, supersensitizing agent | pages 23 to 24 | page 648 (right column) to page 649 (right column) |
| 4. | Brightening agent | page 24 | |
| 5. | Anti-fogging agent and stabilizer | pages 24 to 25 | from page 649 (right column) |
| 6. | Light absorbing agent, filter dye, UV absorber | pages 25 to 26 | page 649 (right column) to page 650 (left column) |
| 7. | Stain inhibitor | page 25 (right column) | page 650 (left and right columns) |
| 8. | Dye image stabilizer | page 25 | |
| 9. | Hardening agent | page 26 | page 651 (left column) |
| 10. | Binder | page 26 | page 651 (left column) |
| 11. | Plasticizer, lubricant | page 27 | page 650 (right column) |
| 12. | Coating aid, surfactant | pages 26 to 27 | page 650 (right column) |
| 13. | Antistatic agent | page 27 | page 650 (right column) |

It is preferred that compounds described in U.S. Pat. Nos. 4,411,987 and 4,435,503 and added to the photographic materials. These compounds are reacted with formaldehyde to fix it and thereby prevent the photographic performance from being deteriorated by formaldehyde gas.

Various color couplers can be used in the present invention. Examples thereof are described in the patent specifications cited in the above *Research Disclosure* (RD) No. 17643, VII-C to G.

Preferred examples of yellow couplers other than the compounds of formula (I) according to the present invention include those described in U.S. Pat. Nos. 3,933,501, 4,022,620, 4,326,024, 4,401,752 and 4,248,961, JP-B-58-10739, U.K. Pat. Nos. 1,425,020 and 1,476,760, U.S. Pat. Nos. 3,973,968, 4,314,023 and 4,511,649 and European Patent 249,473A.

5-Pyrazolone compounds and pyrazoloazole compounds are preferred as magenta couplers. There are particularly preferred magenta couplers described in U.S. Pat. Nos. 4,310,619 and 4,351,897, European Patent 73,636, U.S. Pat. Nos. 3,061,432 and 3,725,067, *Research Disclosure* No. 24220 (June 1984), JP A-60-33552, *Research Disclosure* No. 24230 (June 1984), JP A 60-43659, JP-A-61-72238, JP-A-60-35730, JP-A-55 118024, JP-A-60-185951, U.S. Pat. Nos. 4,500,630, 4,540,654 and 4,556,630 and PCT-WO 88/04795.

Examples of cyan couplers include phenol couplers and naphthol couplers. Preferred cyan couplers are described in U.S. Pat. Nos. 4,052,212, 4,146,396, 4,228,233, 4,296,200, 2,369,929, 2,801,171, 2,772,162, 2,895,826, 3,772,002, 3,758,308, 4,334,011 and 4,327,173, West German Patent Laid-Open No. 3,329,729, European Patents 121,365A and 249,453A, U.S. Pat. Nos. 3,446,622, 4,333,999, 4,775,616, 4,451,559, 4,427,767, 4,690,889, 4,254,212 and 4,296,199 and JP-A-61-42658.

Preferred examples of colored couplers for correcting the unnecessary absorption of colored dyes are described in *Research Disclosure* No. 17643, VII-G, U.S. Pat. Nos. 4,163,670, JP-B-57-39413, U.S. Pat. Nos. 4,004,929 and 4,138,258 and U.K. Patent 1,146,368. Further, preferably used couplers include those couplers which correct the unnecessary adsorption of colored dyes by releasing a fluorescent dye during coupling as described in U.S. Pat. Nos. 4,774,181 and couplers having, as an elimination group, a dye precursor group capable of reacting with a developing agent to form a dye as described in U.S. Pat. No. 4,777,120.

Preferred examples of couplers forming colored dyes having appropriate diffusibility are those described in U.S. Pat. No. 4,366,237, U.K. Patent 2,125,570, European Patent 96,570 and West German Patent Laid Open No. 3,234,533.

Typical examples of dye-forming polymer couplers are described in U.S. Pat. Nos. 3,451,820, 4,080,211, 4,367,282, 4,409,320 and 4,575,910 and U.K. Patent 2,102,173.

Couplers which release a photographically useful residue with coupling can preferably be used in the present invention. Preferred examples of DIR couplers which release a restrainer are those described in patent specifications cited in the above RD 17643, item VII-F, JP-A-57-151944, JP-A-57-154234, JP-A-60-184248, JP-A-63-37346, JP-A-63-37350, U.S. Patents 4,248,962 and 4,782,012.

Preferred examples of couplers which release imagewise a nucleating agent or a development accelerator during development are those described in U.K. Patents 2,097,140 and 2,131,188, JP-A-59-157638 and JP-A-59 170840.

Examples of other couplers which can be used in the photographic materials of the present invention include competitive couplers described in U.S. Pat. No. 4,130,427; polyquivalent type couplers described in redox compound-releasing couplers, DIR coupler-releasing couplers, DIR coupler-releasing redox couplers or DIR redox-releasing compounds described in JP A-60-185950 and JP-A-62-24252; couplers releasing dyes capable of again being colored after elimination described in European Patents 173,302A and 313,308A; bleaching accelerator-releasing couplers described in RD No. 11449, RD No. 24241 and U.S. Pat. No. 4,453,477; ligand-releasing couplers described in JP-A-61 201247; leuco dye-releasing couplers described in JP-A-63-75747; and fluorescent dye-releasing couplers described in U.S. Pat. No. 4,774,181.

The couplers which are used in the present invention can be introduced into the photographic materials by various known methods.

Examples of high-boiling solvents which are used in oil in-water dispersion methods are described in U.S. Pat. No. 2,322,027.

Examples of high-boiling organic solvents which have a boiling point of not lower than 175° C. under atmospheric pressure and are used in oil-in-water dispersion methods include phthalic esters (e.g., dibutyl phthalate, dicyclohexyl phthalate, di-2-ethylhexyl phthalate, decyl phthalate, bis(2,4-di-t-amylphenyl) phthalate, bis(2,4-di-t-amylphenyl) isophthalate, bis(1,1-diethylpropyl) phthalate); phosphoric esters or phosphonic esters (e.g., triphenyl phosphate, tricresyl phosphate, 2-ethylhexyl diphenyl phosphate, tricyclohexyl phosphate, tri-2-ethylhexyl phosphate, tridecyl phosphate, tributoxyethyl phosphate, trichloropropyl phosphate, di-2-ethylhexyl phenyl phosphate); benzoic esters (e.g., 2-ethylhexyl benzoate, dodecyl benzoate, 2-ethylhexyl p-hydroxybenzoate); amides (e.g., N,N-diethyldodecanamide, N,N-diethyllaurylamide, N-tetradecylpyrrolidone); alcohols and phenols (e.g., isostearyl alcohol, 2,4-di-tertamylphenol); aliphatic carboxylic acid esters (e.g., bis(2-ethylhexyl) sebacate, dioctyl azelate, glycerol tributyrate, isostearyl lactate, trioctyl citrate); aniline derivatives (e.g., N,N-dibutyl-2-butoxy-5-tertoctylaniline); and hydrocarbons (e.g., paraffin, dodecylbenzene, diisopropylnaphthalene). As auxiliary-solvents, there can be used organic solvents having a boiling point of not lower than about 30° C., preferably not lower than 50° C., but not higher than 160° C. Typical examples of the auxiliary-solvents include butyl acetate, ethyl propionate, methylethyl ketone, cyclohexanone, 2-ethoxyethyl acetate and dimethylformamide.

Examples of latex dispersing stages, the effect thereof and impregnating latexes are described in U.S. Pat. No. 4,199,363 and West German Patent Application (OLS) Nos. 2,541,274 and 2,541,230.

It is preferred that the color photographic materials of the present invention contain antiseptics or antifungal agents such as 1,2-benzisothiazoline-3-one, n-butyl p-hydroxybenzoate, phenol, 4-chloro-3,5-dimethylphenol, 2-phenoxyethanol and 2-(4 thiazolyl)benzimidazole.

The present invention can be applied to various color photographic materials. Typical examples of the color photographic materials to which the present invention can be applied include general-purpose and movie color negative films, reversal color films for slide and TV, color paper, color positive films and reversal color paper.

Examples of supports which can be used in the present invention are described in the above described RD No. 17643 (page 28) and RD No. 18716 (right column of page 647 to left column of page 648).

In the photographic materials of the present invention, the sum total of the layer thickness of the entire hydrophilic colloid layers on the side on which the emulsion layers are provided is preferably not larger than 28 μm, more preferably not larger than 23 μm, and even more preferably not larger than 20 μm. The layer-swelling rate $T_{\frac{1}{2}}$ is preferably not longer than 30 seconds, more preferably not longer than 20 seconds. The layer thickness refers to a layer thickness obtained by measuring the thickness at 25° C. and RH of 55% (under air conditioning for two days). The layer swelling rate $T_{\frac{1}{2}}$ can be measured by known methods in the field of photography. For example, the swelling rate can be measured by using a swelling meter described in A. Green, Photogra. Sci. Eng., Vol. 19, No. 2, pp. 124 to 129. The swelling rate $T_{\frac{1}{2}}$ is defined by the time taken for reaching ½ of the saturated layer thickness which means 90% of the maximum swelling layer thickness when processed with a color developing solution at 30° C. for 3¼ minutes.

The layer swelling rate $T_{\frac{1}{2}}$ can be controlled by adding a hardening agent to the gelatin as a binder or by changing the conditions with time after coating. The swelling ratio is preferably 150 to 400%. The swelling ratio can be calculated from the formula (maximum swelling layer thickness-layer thickness)/layer thickness wherein the maximum swelling layer thickness is as defined above.

The color photographic materials according to the present invention can be processed according to the general methods described in the above described RD No. 17643 (pp. 28 to 29) and RD No. 18716 (left column to right column of page 615).

The color developing solutions which can be used in the present invention are preferably aqueous alkaline solutions composed mainly of aromatic primary amine color developing agents. Aminophenol compounds are useful as the color developing agents and p-phenylenediamine compounds are preferred as the color developing agents. Typical examples thereof include 3-methyl-4-amino-N,N-diethylaniline, 3-methyl-4-amino-N-ethyl-N-β-hydroxyethylaniline, 3-methyl-4-amino-N-ethyl-N-β-methanesulfonamidoethylaniline, 3-methyl-4-amino-N-ethyl-N-β-methoxyethylaniline and salts thereof such as sulfate, hydrochloride and p-toluenesulfonate. Among them, 3-methyl-4 amino-N-ethyl-N-β-hydroxyethylaniline sulfate is particularly preferred. These compounds may be used either alone or in combination of two or more thereof.

Generally, the color developing solutions contain pH buffering agents such as alkali metal carbonates, borates and phosphates, restrainers such as chlorides, bromides, iodides, benzimidazoles, benzothiazoles and mercapto compounds and anti-fogging agents. If desired, the color developing solutions may optionally contain preservatives such as hydroxylamine, diethylhydroxylamine, sulfites, hydrazine such as phenylsemicarbazides, triethanolamine, catecholsulfonic acids; organic solvents such as ethylene glycol and diethylene glycol; development accelerators such as benzyl alcohol, polyethylene glycol, quaternary ammonium salts and amines; color forming couplers, competitive couplers and auxiliary developing agents such as 1-phenyl-3-pyrazolidone; tackifiers; and chelating agents such as polyaminocarboxylic acids, polyaminophosphonic acids, alkylphosphonic acids and phosphonocarboxylic acids, for example, ethylenediaminetetraacetic acid, nitrotriacetic acid, diethylenetriaminepentaacetic acid, cyclohexanediaminetetraacetic acid, hydroxyethylimidinoacetic acid, 1-hydroxyethylidene 1,1-diphosphonic acid, nitrilo-N,N,N-trimethylenephosphonic acid, ethylenediamine-N,N,N',N'-tetramethylenephosphonic acid and ethylenediamine-di(o-hydroxyphenylacetic acid) and salts thereof.

Generally, when reversal processing is to be conducted, black-and-white development is first carried out and color development is then carried out. Black and-white developing solutions may contain conventional developing agents such as dihydroxybenzenes (e.g., hydroquine), 3-pyrazolidones (e.g., 1-phenyl-3-pyrazolidone) and aminophenols (e.g., N-methyl-p-aminophenol). These developing agents may be used either alone or in combination of two or more thereof.

The pH of the color developing solutions and the black-and-white developing solutions is generally in the range of 9 to 12. The replenishment rate of these developing solutions varies depending on the type of the color photographic materials, but the replenishment rate is usually not more than 3 l per m² of the photographic material. The replenishment rate can be reduced to 500 ml of less when the concentration of bromide ion in the replenisher is reduced. When the replenishment is to be reduced, it is desirable that the contact area of the layer to be processed with air is reduced to prevent the solution from being evaporated or oxidized by the air.

The contact area of the processing solution with air in the processing tank can be represented by the opening ratio defined below.

$$\text{Opening ratio} = \frac{\text{Contact area (cm}^2\text{) of processing solution with air}}{\text{Volume (cm}^3\text{) of processing solution}}$$

It is preferred that the opening ratio is not higher than 0.1, more preferably in the range of 0.001 to 0.05. Methods for reducing the opening ratio include a method wherein a masking material such as a floating lid is provided on the surface of the processing solution in the processing tank; a method wherein a movable lid is provided as described in JP-A-1-82033; and a slit processing method as described in JP-A-63-216050. It is preferred that the reduction of the opening ratio is applied to both stages of color development and black-and-white development as well as all subsequent stages such as bleaching, bleach-fixing, fixing, rinsing and stabilization. The replenishment rate can be reduced by using a means for inhibiting the accumulation of bromide ion in the developing solution.

The color development time is usually set for 2 to 5 minutes. The processing time can be further shortened by conducting the development at a higher temperature and higher pH by using the color developing agent at a higher concentration.

After color development, the photographic emulsion layer is generally bleached. Bleaching may be carried out simultaneously with fixing (bleach fix treatment) or they may be carried out separately. After bleaching, a bleach-fix treatment may be conducted to expedite processing. Treatment may be conducted with a bleach-fix bath composed of two consecutive tanks. Fixing may be conducted before the bleach-fix treatment. After the bleach-fix treatment, bleaching may be conducted according to the desired purpose. Examples of bleaching agents include compounds of polyvalent metals such as iron(III), peracids, quinones and nitro compounds. Typical examples of the bleaching agents include organic complex salts of iron(III) such as complex salts of polyaminocarboxylic acids (e.g., ethylenediaminetetraacetic acid, diethylenetriaminepentaacetic acid, cyclohexanediaminetetraacetic acid, methyliminodiacetic acid, 1,3-diaminopropanetetraacetic acid, glycol ether diaminetetraacetic acid, etc.) citric acid, tartaric acid, malic acid, etc. Among them, iron(III) complex salts of polyaminocarboxylic acids such as (ethylenediaminetetraacetonato)iron(III) complex and (1,3-diaminopropanetetraacetonato)iron(III) complex are preferred from the viewpoint of rapid processing and prevention of environmental pollution. Further, iron(III) complex salts of polyaminocarboxylic acids are useful for bleaching solutions and bleach-fix solutions. The pH of the bleaching solutions containing the iron(III) complex salts of the polyaminocarboxylic acids and the bleach-fix solutions containing said iron(III) complex salts is generally in the range of 4.0 to 8. Lower pH may be used to expedite processing.

If desired, the bleaching solution, the bleach-fix solution and the pre-bath thereof may contain bleaching accelerators. Examples of the bleaching accelerators include compounds having a mercapto group or a disulfide group described in U.S. Pat. No. 3,893,858, West German Patents 1,290,812 and 2,059,988, JP-A-53-32736, JP-A-53-57831, JP-A-53-37418, JP-A-53-72623, JP-A-53-95630, JP-A-53-95631, JP-A-53-104232, JP-A-53-124424, JP-A-53-141623, JP-A-53-28426 and *Research Disclosure* No. 17129 (July 1978); Thiazolidine derivatives described in JP-A-50-140129; thiourea derivatives described in JP-B-45-8506, JP-A-52-20832, JP-A-53-32735 and U.S. Pat. No. 3,706,561; iodides described in West German Patent 1,127,715 and JP-A-58-16235; polyoxyethylene compounds described in West German Patents 996,410 and 2,748,430; polyamine compounds described in JP-B-45-8836; compounds described in JP-A-49-42434, JP-A-49-59644, JP-A-53-94927, JP-A-54-35727, JP-A-55-26506 and JP-A-58-163940; and bromide ions. Among them, the compounds having a mercapto group or a disulfide group are preferred from the viewpoint of high accelerating effect. Particularly, the compounds described in U.S. Pat. No. 3,893,858, West German patent 1,290,812 and JP-A 53-95630 are preferred. Further, the compounds described in U.S. Pat. No. 4,552,834 are preferred. These bleaching accelerators may be incorporated in the photographic materials. These bleaching accelerators are particularly effective in conducting the bleach-fixing of the color photographic materials for photography.

It is preferred that in addition to the abovedescribed compounds, the bleaching solutions and the bleach-fix solutions contain organic acid to prevent stain from being caused by bleaching. Compounds having a dissociation constant (pka) of 2 to 5 are particularly preferred. Examples of suitable organic acids include acetic acid and propionic acid.

Examples of fixing agents for use in the fixing solutions and the bleach-fix solutions include thiosulfates, thiocyanates, thioether compounds, thioureas and many iodides. The thiosulfates are widely used and particularly ammonium thiosulfate is most widely used. Combinations of the thiosulfates with the thioether compounds and thioureas are preferred. Sulfites, bisulfites, carbonyl-bisulfites adducts or sulfinic compounds described in European Patent 94769A are preferred as preservatives for the fixing solutions and the bleach-fix solutions. Further, it is preferred that the fixing solutions and the bleach-fix solutions contain aminopolycarboxylic acids or organic phosphonic acids for the purpose of stabilization. A shorter desilverization time (in total) is preferred, so long as no defect in desilverization is caused. Preferred desilverization time is one to three minutes, more preferably one to two minutes. The processing temperature is 25° to 50° C., preferably 35° to 45° C. When desilverization is carried out within the preferred temperature range, the desilverization rate is improved and stain is effectively prevented from being caused after treatment.

It is preferred that stirring is conducted as vigorously as possible in the desilverization stage. Examples of methods for vigorously conducting stirring include a method wherein the jet stream of the processing solution is allowed to collide with the emulsion surface of the photographic material as described in JP-A-62-183460 and JP-A-62-183461; a method wherein a rotating means is used to enhance the stirring effect as described in JP-A-62-183461; a method wherein the photographic material is moved while contacting the emulsion surface thereof with a wiper blade provided in the solution to thereby form turbulent flow on the emulsion surface, whereby stirring offset is improved; and a method wherein the amount of the processing solution to be wholly circulated is increased. These methods for improving stirring can be effectively used for the bleaching solution, the bleachfix solution and the fixing solution. It is thought that an improvement in stirring increases the flow of the bleaching agent and the fixing agent to the emulsion layer and as a result, the rate of desilverization is enhanced. When the bleaching accelerators are used, the above stirring-improving means are more effective and the accelerating effect can be greatly increased or the problem of inhibiting fixation caused by the bleaching accelerators can be solved.

It is preferred that automatic processors for use in the processing of the photographic materials of the present invention are provided with photographic material-conveying means described in JP-A-60-191257, JP-A-60-191258 and JP-A-60-191259. The conveying means can greatly reduce the amount of the processing solution brought over from the previous bath to the subsequent bath and have a remarkable effect of preventing the performance of the processing solution from being deteriorated. Such an effect is particularly effective in shortening the processing time in each stage and in reducing the replenishment rate of the processing solution.

Usually, the silver halide color photographic materials of the present invention are subjected to the washing and/or stabilization stage after desilverization. The amount of rinsing water in the washing stage varies widely depending on the characteristics (e.g., depending on materials used such as couplers) of the photographic materials, the use, the temperature of the rinsing water, the number of rinsing tanks (the number of stages), the replenishing system (counter-current, direct flow) and other conditions. The relationship between the amount of water and the number of rinsing tanks in the multi-stage counter-current system can be determined by the method described in the Journal of the Society of Motion Picture and Television Engineers, Vol. 64, p. 248 to 253 (May 1955).

According to the multi-stage counter-current system described in the above literature, the amount of the rinsing water can be greatly reduced. However, there is a problem that the residence time of the water in the tanks is prolonged and as a result, bacteria grow and the resulting suspended matter is deposited on the photographic material. A method for reducing calcium ion and magnesium ion described in JP-A-62-288838 can be effectively used for the color photographic materials of the present invention to solve the above-mentioned problem. Further, isothiazolone compounds, thiabendazole compounds, chlorine-containing germicides such as sodium chlorinated isocyanurate and benztriazole described in JP-A-57-8542 and germicides described in Chemistry of Germicidal Antifungal Agent, written by Hiroshi Horiguchi, (1986) Sankyo Shuppan), Sterilization, Disinfection, Antifungal Technique (1982), edited by Sanitary Technique Society and Antibacterial and Antifungal cyclopedie (1986), edited by Nippon Antibacterial Antifungal Society, can be used.

The pH of the rinsing water in the treatment of the photographic materials of the present invention is in the range of 4 to 9, preferably 5 to 8. The temperature of the rinsing water and the washing time vary depending on the characteristics of the photographic materials, the use, etc., but the temperature and time of washing are generally 15° to 45° C. for 20 seconds to 10 minutes, preferably 25° to 40° C. for 30 seconds to 5 minutes. The photographic materials of the present invention may be processed directly with stabilizing solutions in place of the rinsing water. Such stabilizing treatment can be carried out by conventional methods described in JP-A-57-8543, JP-A-58-14834 and JP-A-60-220345.

Stabilizing treatment subsequent to rinsing may be conducted. The stabilizing treatment may be used as the final bath for the color photographic materials. An example thereof includes a stabilizing bath containing a dye image stabilizer and a surfactant. Examples of the dye image stabilizer include aldehydes such as formalin and glutaric aldehyde, N-methylol compounds, hexamethylenetetraamine and aldehyde sulfurous acid adducts. The stabilizing bath may contain various chelating agents and antifungal agents.

Overflow solution from the replenishment of the rinsing water and/or stabilizing solution can be reused in other stages such as in the desilverization stage.

It is preferred that when each processing solution is concentrated by evaporation during the above processing using automatic processors, etc., water is added to each processing solution to replenish the amount evaporated.

The color developing agents may be incorporated in the silver halide color photographic materials of the present invention for the purpose of simplifying and expediting processing. It is preferred that precursors for the color developing agents are used for the incorporation thereof in the photographic materials. Examples of the precursors include indoaniline compounds described in U.S. Pat. No. 3,342,597; Schiff base compounds described in U.S. Pat. No. 3,342,599 *Research Disclosure* No. 14850 and ibid., No. 15159; aldol compounds described in *Research Disclosure* No. 13924; metal complex salts described in U.S. Pat. No. 3,719,492; and urethane compounds described in JP-A 53-135628.

If desired, 1-phenyl-3-pyrazolidones may be incorporated in the silver halide color photographic materials of the present invention for the purpose of accelerating color development. Typical examples of such compounds include those described in JP-A-56-64339, JP-A-57-144547 and JP-A 58-115438.

In the present invention, various processing solutions are used at a temperature of 10° to 50° C. Generally, a temperature of 33° to 38° C. is used. However, it is possible that a higher temperature is used to accelerate processing and to shorten the processing time, while a lower temperature is used to improve the image quality and to improve the stability of the processing solutions. If desired, treatments using cobalt intensification or hydrogen peroxide intensification described in West German Patent 2,226,770 and U.S. Pat. No. 3,674,499 may be carried out to save silver.

The silver halide photographic materials of the present invention can be applied to heat developing photosensitive materials described in U.S. Pat. No. 4,500,626, JP-A-60-133449, JP-A 59-218443, JP-A-61-238056 and European Patent 210,660A2.

The present invention is now illustrated in greater detail by reference to the following examples which, however, are not to be construed as limiting the invention in any way.

EXAMPLE 1

A cellulose triacetate film support having a subbing applied thereto was coated with the following layers having the following compositions to prepare a multilayer color photographic material as sample 101.

Composition of sensitive layers

The coating weight for each of the silver halide and the colloidal silver is represented by $g/m^2$ in terms of silver. The coating weight of each of the couplers, additives and gelatin is represented by $g/m^2$. The amount of each sensitizing dye is represented by moles per mole of silver halide in the same layer. The following abbreviations represent the following materials. When a material has a plurality of functions, one of them typifies the material.

| | |
|---|---|
| UV: | ultraviolet light absorber |
| Solv: | high-boiling organic solvent |
| ExF: | dye |
| ExS: | sensitizing dye |
| ExC: | cyan coupler |
| ExM: | magenta coupler |
| ExY: | yellow coupler |
| Cpd: | additive |

First Layer (antihalation layer)

| | |
|---|---|
| Black colloidal silver | 0.15 |
| Gelatin | 2.0 |
| ExM-6 | 0.2 |
| UV-1 | 0.03 |
| UV-2 | 0.06 |
| UV-3 | 0.07 |
| Solv-1 | 0.3 |
| Solv-2 | 0.08 |
| ExF-1 | 0.01 |
| ExF-2 | 0.01 |
| ExF-3 | 0.005 |
| Cpd-6 | 0.001 |

Second Layer (low-sensitivity red-sensitive emulsion layer)

| | |
|---|---|
| Silver iodobromide emulsion [AgI: 4 mol %, uniform AgI type, diameter (in terms of sphere): 0.4 μm, coefficient of variation (in terms of sphere): 30%, tabular grains, ratio of diameter/thickness: 3.0] | 0.37 (as silver) |
| Silver iodobromide emulsion [AgI: 6 mol %, interior high AgI type (core shell ratio = 2:1), diameter (in terms of sphere): 0.45 μm, coefficient of variation (in terms of sphere): 23%, tabular grains, ratio of diameter/thickness: 2.0] | 0.19 (as silver) |
| Gelatin | 0.8 |
| ExS-1 | $2.3 \times 10^{-4}$ |
| ExS-2 | $1.4 \times 10^{-4}$ |
| ExS-5 | $2.3 \times 10^{-4}$ |
| ExS-7 | $4.2 \times 10^{-6}$ |
| ExC-1 | 0.17 |
| ExC-2 | 0.03 |
| ExC-3 | 0.009 |

Third Layer (medium-sensitivity red-sensitive emulsion layer)

| | |
|---|---|
| Silver iodobromide emulsion [AgI: 6 mol %, interior high AgI type (core shell ratio = 2:1), diameter (in terms of sphere): 0.65 μm, coefficient of variation (in terms of sphere): 28%, tabular grains, diameter/thickness ratio: 2.0] | 0.65 (as silver) |
| Gelatin | 1.0 |
| ExS-1 | $2.3 \times 10^{-4}$ |
| ExS-2 | $1.4 \times 10^{-4}$ |
| ExS-5 | $2.3 \times 10^{-4}$ |
| ExS-7 | $4.2 \times 10^{-6}$ |
| ExC-1 | 0.31 |
| ExC-2 | 0.01 |
| ExC-3 | 0.10 |

Fourth Layer (high-sensitivity red-sensitive emulsion layer)

| | |
|---|---|
| Silver iodobromide emulsion [AgI: 9.3 mol %, multiple structural grains (core shell ratio = 3:4:2), AgI content: in order of 24.0 mol % (the interior), 0 mol % and 6 mol %, diameter (in terms of sphere): 0.75 μm, coefficient of variation (in terms of sphere): 23%, tabular grains, diameter/thickness ratio: 2.5] | 1.5 (as silver) |
| Gelatin | 1.4 |
| ExS-1 | $1.9 \times 10^{-4}$ |
| ExS-2 | $1.2 \times 10^{-4}$ |
| ExS-5 | $1.9 \times 10^{-4}$ |
| ExS-7 | $8.0 \times 10^{-6}$ |
| ExC-1 | 0.08 |
| ExC-4 | 0.09 |
| Solv-1 | 0.08 |
| Solv-2 | 0.20 |
| CpD-7 | $4.6 \times 10^{-4}$ |

Fifth Layer (interlayer)

| | |
|---|---|
| Gelatin | 0.6 |
| Cpd-1 | 0.1 |
| Polyethyl acrylate latex | 0.08 |
| Solv-1 | 0.08 |

Sixth Layer (low-sensitivity green-sensitive emulsion layer)

| | |
|---|---|
| Silver iodobromide emulsion [AgI: 4 mol %, uniform AgI type, diameter (in terms of sphere): 0.33 μm, | 0.18 (as silver) |

| | |
|---|---|
| coefficient of variation (in terms of sphere): 37%, tabular grains, diameter/thickness ratio: 2.0] | |
| Gelatin | 0.4 |
| ExS-3 | $1.6 \times 10^{-4}$ |
| ExS-4 | $4.8 \times 10^{-4}$ |
| ExS-5 | $1 \times 10^{-4}$ |
| ExM-5 | 0.16 |
| ExM-7 | 0.03 |
| ExY-8 | 0.01 |
| Solv-1 | 0.06 |
| Solv-4 | 0.01 |
| Seventh Layer (medium-sensitivity green-sensitive emulsion layer) | |
| Silver iodobromide emulsion [AgI: 4 mol %, uniform AgI type, diameter (in terms of sphere): 0.55 μm, coefficient of variation (in terms of sphere): 15%, tabular grains, diameter/thickness ratio: 4.0] | 0.27 (as silver) |
| Gelatin | 0.6 |
| ExS-3 | $2 \times 10^{-4}$ |
| ExS-4 | $7 \times 10^{-4}$ |
| ExS-5 | $1.4 \times 10^{-4}$ |
| ExM-5 | 0.17 |
| ExM-7 | 0.04 |
| ExY-8 | 0.04 |
| Solv-1 | 0.14 |
| Solv-4 | 0.01 |
| Eighth Layer (high-sensitivity green-sensitive emulsion layer) | |
| Silver iodobromide emulsion [AgI: 8.8 mol %, multi-layer structural grains having a silver amount ratio of 3:4:2, AgI content: in order of 24 mol % (the interior), 0 mol % and 3 mol %, diameter (in terms of sphere): 0.75 μm, coefficient of variation (in terms of sphere): 23%, tabular grains, diameter/thickness ratio: 1.6] | 0.5 (as silver) |
| Gelatin | 0.6 |
| ExS-4 | $5.2 \times 10^{-4}$ |
| ExS-5 | $1 \times 10^{-4}$ |
| ExS-8 | $0.3 \times 10^{-4}$ |
| ExM-5 | 0.08 |
| ExM-6 | 0.03 |
| ExY-8 | 0.02 |
| ExC-1 | 0.01 |
| ExC-4 | 0.01 |
| Solv-1 | 0.23 |
| Solv-2 | 0.05 |
| Solv-4 | 0.01 |
| Cpd-7 | $1 \times 10^{-4}$ |
| Cpd-8 | 0.01 |
| Ninth Layer (interlayer) | |
| Gelatin | 0.6 |
| Cpd-1 | 0.04 |
| Polyethyl acrylate latex | 0.05 |
| Solv-1 | 0.02 |
| UV-4 | 0.03 |
| UV-5 | 0.04 |
| Tenth Layer (donor layer having a multi-layer effect on red-sensitive layer) | |
| Silver iodobromide emulsion [AgI: 8 mol %, interior high AgI type having core shell ratio of 2:1, diameter (in terms of sphere): 0.65 μm, coefficient of variation (in terms of sphere): 25%, tabular grains, diameter/thickness ratio: 2.0] | 0.72 (as silver) |
| Silver iodobromide emulsion [AgI: 4 mol %, uniform AgI type, diameter (in terms of sphere): 0.4 μm, coefficient of variation (in terms of sphere): 30%, tabular grains, diameter/thickness ratio: 3.0] | 0.21 (as silver) |
| Gelatin | 1.0 |
| ExS-3 | $6 \times 10^{-4}$ |
| ExM-10 | 0.19 |
| Solv-1 | 0.30 |
| Solv-6 | 0.03 |
| Eleventh Layer (yellow filter layer) | |
| Yellow colloidal silver | 0.06 |
| Gelatin | 0.8 |
| Cpd-2 | 0.13 |
| Solv-1 | 0.13 |
| Cpd-1 | 0.07 |
| Cpd-6 | 0.002 |
| H-1 | 0.13 |
| Twelfth Layer (low-sensitivity blue-sensitive emulsion layer) | |
| Silver iodobromide emulsion [AgI: 4.5 mol %, uniform AgI type, diameter (in terms of sphere): 0.7 μm, coefficient of variation (in terms of sphere): 15%, tabular grains, diameter/thickness ratio: 7.0] | 0.45 (as silver) |
| Silver iodobromide emulsion [AgI: 3 mol %, uniform AgI type, diameter (in terms of sphere): 0.3 μm, coefficient of variation (in terms of sphere): 30%, tabular grains, diameter/thickness ratio: 7.0] | 0.25 (as silver) |
| Gelatin | 2.1 |
| ExS-6 | $9 \times 10^{-4}$ |
| ExC-1 | 0.13 |
| ExC-4 | 0.03 |
| ExY-9 | 0.16 |
| ExY-11 | 1.04 |
| Solv-1 | 0.51 |
| Thirteenth Layer (interlayer) | |
| Gelatin | 0.4 |
| ExY-12 | 0.20 |
| Solv-1 | 0.19 |
| Fourteenth Layer (high-sensitivity blue-sensitive emulsion layer) | |
| Silver iodobromide emulsion [AgI: 10 mol %, interior high AgI type diameter (in terms of sphere): 1.0 μm, coefficient of variation (in terms of sphere): 25%, multiple twinning tabular grains, diameter/thickness ratio: 2.0] | 0.4 (as silver) |
| Gelatin | 0.5 |
| ExS-6 | $1 \times 10^{-4}$ |
| ExY-9 | 0.01 |
| ExY-11 | 0.20 |
| ExC-1 | 0.01 |
| Solv-1 | 0.10 |
| Fifteenth Layer (first protective layer) | |
| Finely divided silver iodobromide emulsion [AgI: 2 mol %, uniform AgI type, diameter (in terms of sphere): 0.07 μm] | 0.12 (as silver) |
| Gelatin | 0.7 |
| UV-4 | 0.11 |
| UV-5 | 0.16 |
| Solv-5 | 0.02 |
| H-1 | 0.13 |
| Cpd-5 | 0.10 |
| Polyethyl acrylate latex | 0.09 |
| Sixteenth Layer (second protective layer) | |
| Finely divided silver iodobromide emulsion [AgI: 2 mol %, uniform AgI type, diameter (in terms of sphere): 0.07 μm] | 0.36 (as silver) |
| Gelatin | 0.85 |
| Polymethyl methacrylate particles (diameter: 1.5 μm) | 0.2 |
| Cpd-4 | 0.04 |
| W-4 | 0.02 |
| H-1 | 0.17 |

In addition to the above-described ingredients, Cpd-3 (0.07 g/m²) as a stabilizer for the emulsions, and surfactants W-1 (0.006 g/m²), W-2 (0.33 g/m²) and W-3 (0.10 g/m²) as a coating aid or emulsifying dispersant were added to each layer.

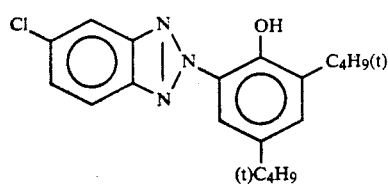
UV-1
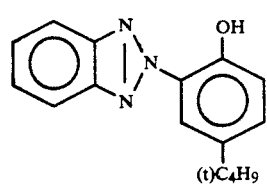
UV-2
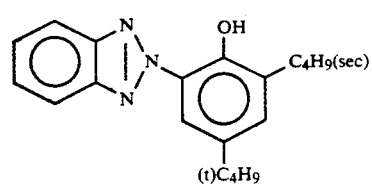
UV-3
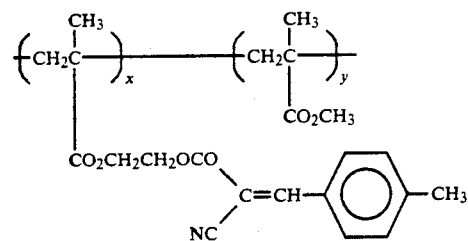
x:y = 70:30 (wt %)
UV-4
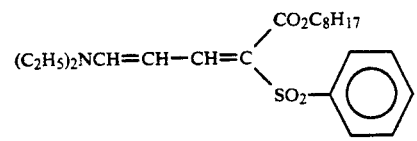
UV-5
Tricresyl phosphate — Solv-1
Dibutyl phthalate — Solv-2
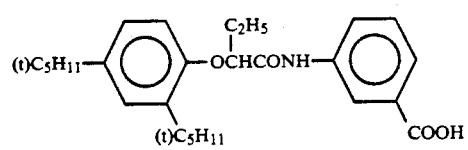
Solv-4
Trihexyl phosphate — Solv-5
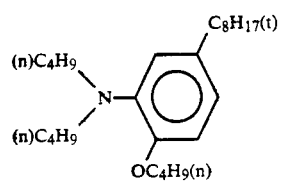
Solv-6

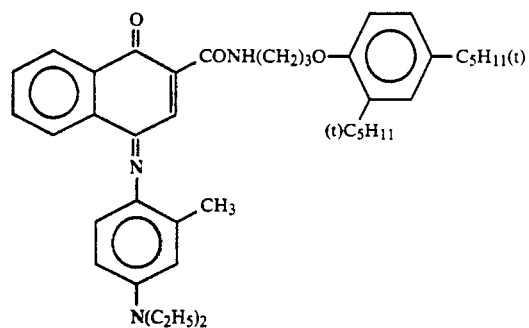
ExF-1
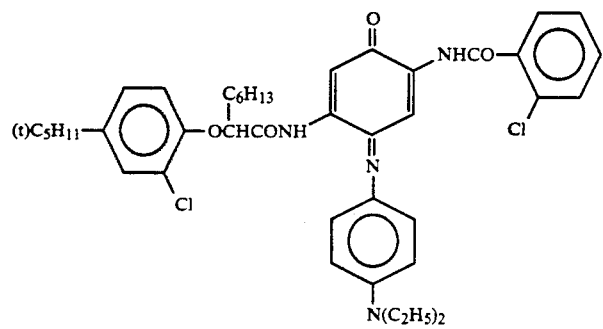
ExF-2
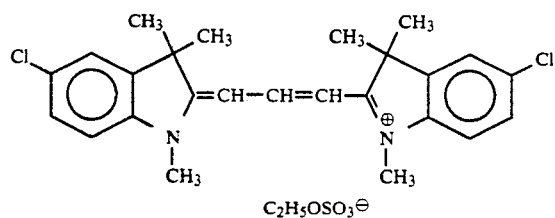
ExF-3
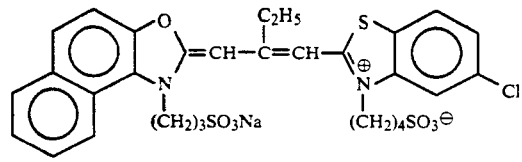
ExS-1
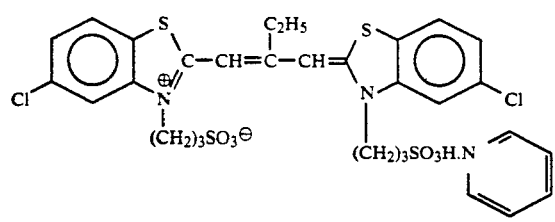
ExS-2
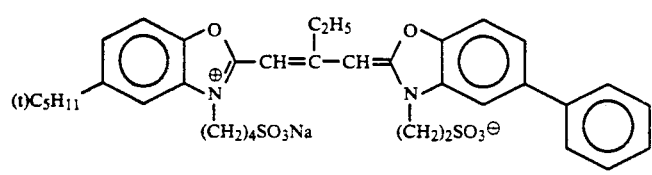
ExS-3
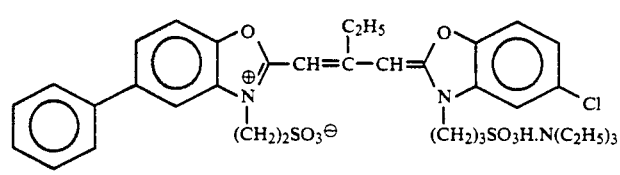
ExS-4

-continued
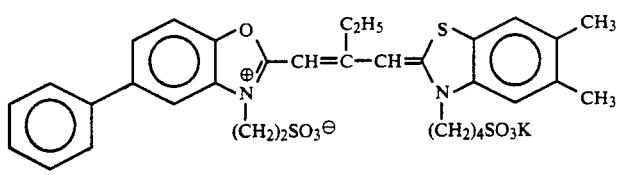 ExS-5
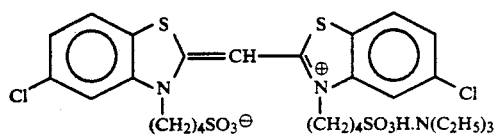 ExS-6
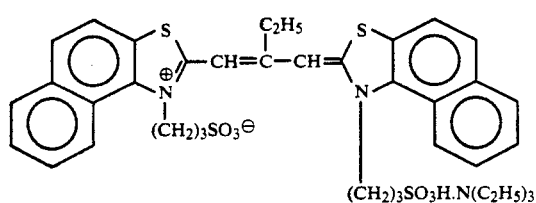 ExS-7
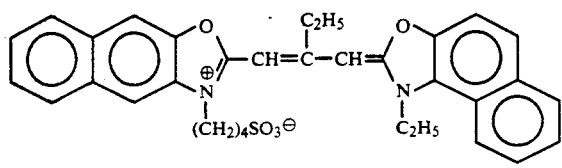 ExS-8
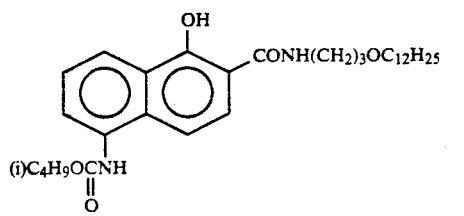 ExC-1
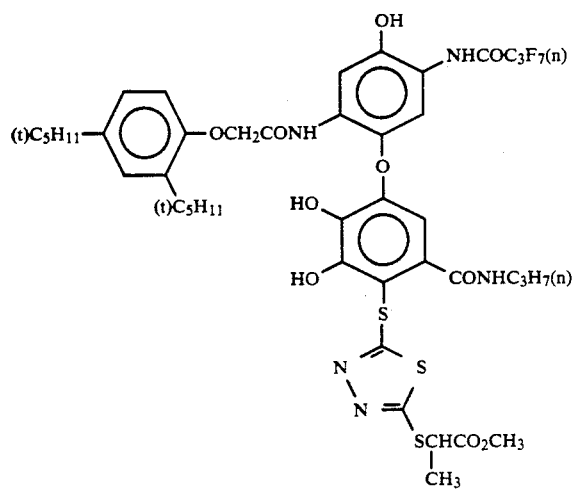 ExC-2

ExC-3
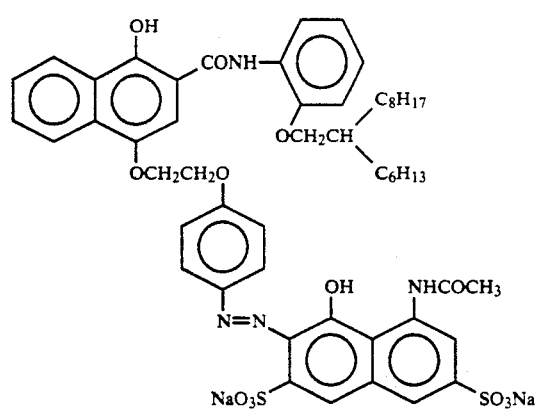
ExC-4
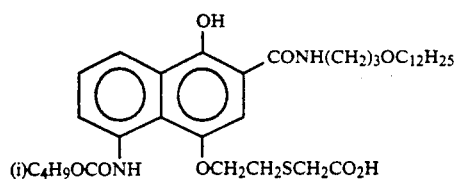
ExM-5
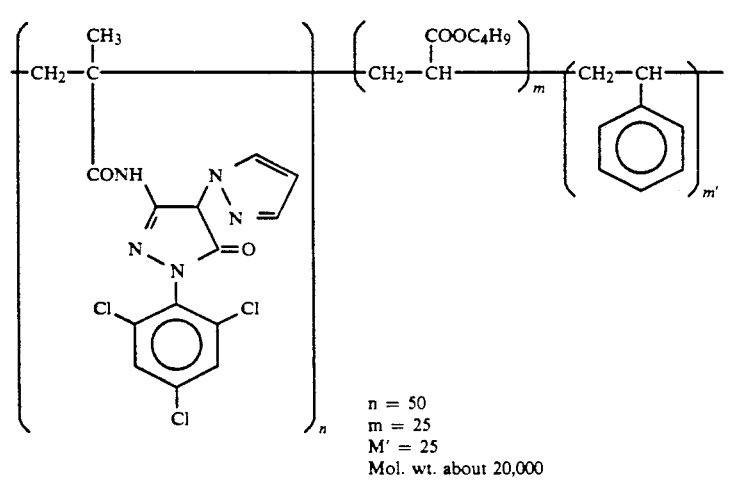
n = 50
m = 25
M' = 25
Mol. wt. about 20,000
ExM-6
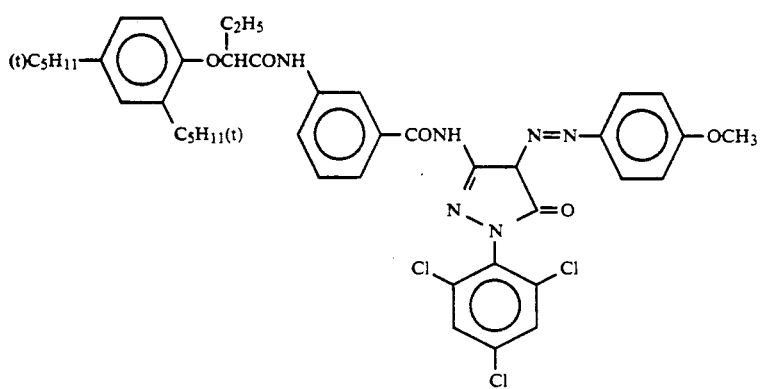

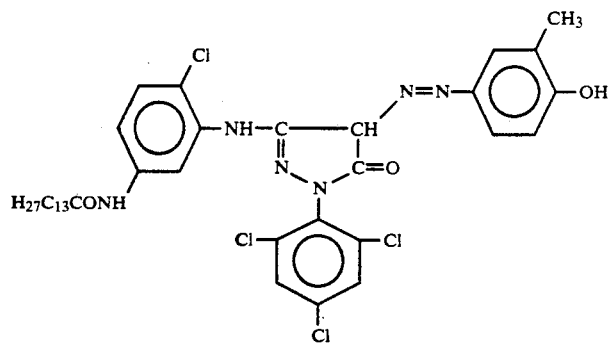
ExM-7
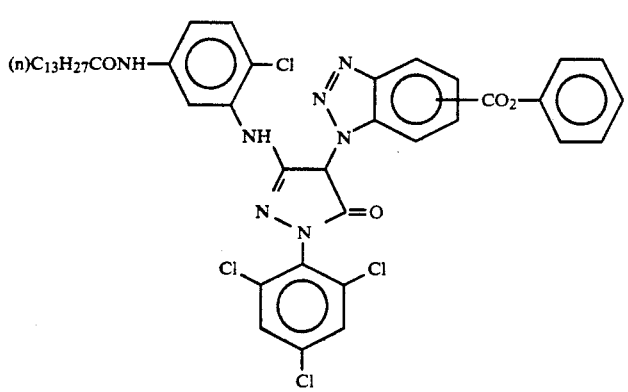
ExM-10
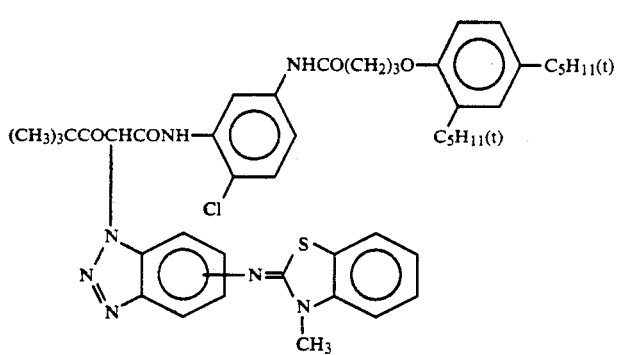
ExY-8
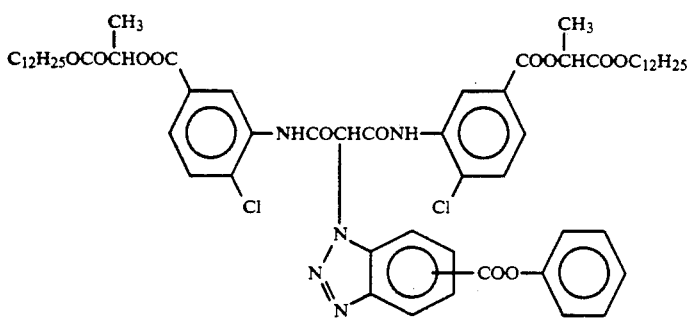
ExY-9
(conventional coupler)

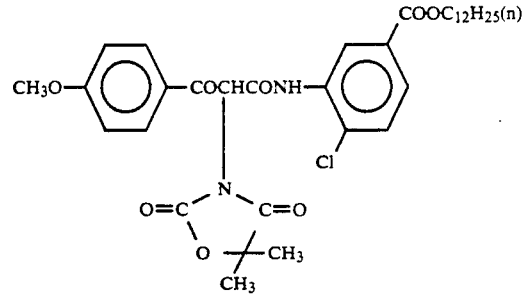
ExY-11
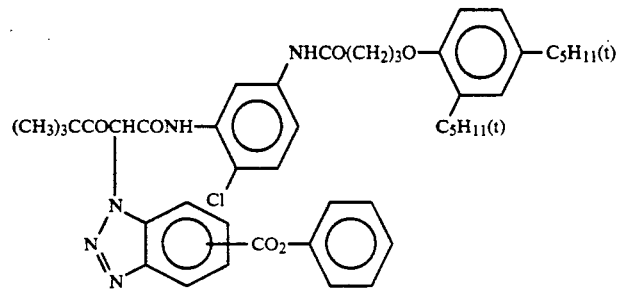
ExY-12
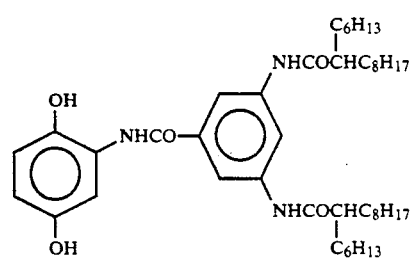
Cpd-1
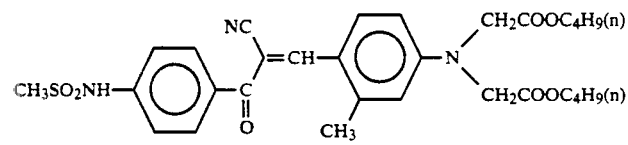
Cpd-2
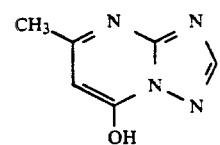
Cpd-3
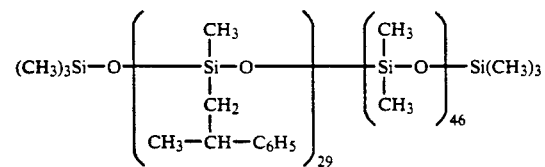
Cpd-4
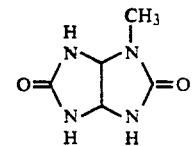
Cpd-5
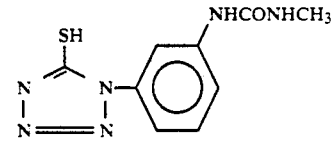
Cpd-6

Cpd-7

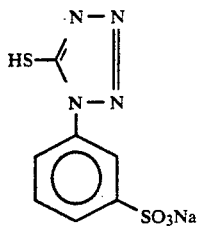

Cpd-8

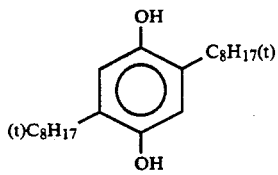

H-1

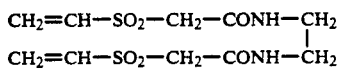

W-1

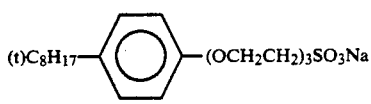

W-2

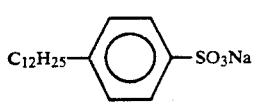

W-3

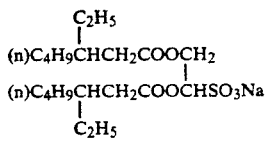

W-4

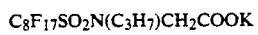

Preparation of samples 102 to 109

Samples 102 to 109 were prepared in the same way as in the preparation of sample 101 except that an equimolar amount of each coupler indicated in Table 1 was added to each of the twelfth layer and the fourteenth layer in place of ExY-11.

The samples 101 to 109 were exposed through a wedge and then subjected to the following processing stages.

| Stage | Processing method | |
|---|---|---|
| | Processing time | Processing temperature (°C.) |
| Color development | 3 min. 15 sec. | 38 |
| Bleaching | 1 min. 00 sec. | 38 |
| Bleach-fix | 3 min. 15 sec. | 38 |
| Rinse (1) | 40 sec. | 35 |
| Rinse (2) | 1 min. 00 sec. | 35 |
| Stabilization | 40 sec. | 38 |
| Drying | 1 min. 15 sec. | 55 |

Each processing solution had the following composition.

| Color developing solution | unit: g |
|---|---|
| Diethylenetriaminepentaacetic acid | 1.0 |
| 1-Hydroxyethylidene-1,1-diphosphonic acid | 3.0 |
| Sodium sulfite | 4.0 |
| Potassium carbonate | 30.0 |
| Potassium bromide | 1.4 |
| Potassium iodide | 1.5 mg |
| Hydroxyamine sulfate | 2.4 |
| 2-(N-Ethyl-N-β-hydroxyethylamino)-2-methylaniline sulfate | 4.5 |
| Add water | To make 1.0 l |
| pH | 10.05 |

| Bleaching solution | unit: g |
|---|---|
| Ethylenediaminetetraacetic acid iron(III) ammonium dihydrate | 120.0 |
| Disodium ethylenediaminetetraacetate | 10.0 |
| Ammonium bromide | 100.0 |
| Ammonium nitrate | 10.0 |
| Bleaching accelerator | 0.005 mol |

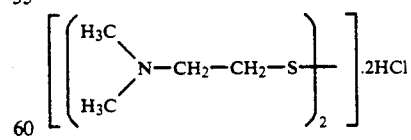

| Ammonia water (27%) | 15.0 ml |
| Add water | To make 1.0 l |
| pH | 6.3 |

| Bleach-fix solution | unit: g |
|---|---|
| Ethylenediaminetetraacetic acid iron(III) ammonium dihydrate | 50.0 |
| Disodium ethylenediaminetetraacetate | 5.0 |
| Sodium sulfite | 12.0 |
| Aqueous solution of ammonium | 240.0 ml |

-continued

| | |
|---|---|
| thiosulfate (70%) | |
| Ammonia water (27%) | 6.0 |
| Add water | To make 1.0 l |
| pH | 7.2 |

Rinsing solution

Tap water was passed through a mixed-bed column packed with an H-type strongly acidic cation exchange resin (Amberlite IR-120B, a product of Rohm & Haas Co.) and an OH-type anion exchange resin (Amberlite IR-400) to reduce the concentration of each of the calcium and magnesium ions to no higher than 3 mg/l. Sodium isocyanurate dichloride (20 mg/l) and sodium sulfate (150 mg/l) were then added thereto.

The pH of the solution was in the range of 6.5 to 7.5.

| Stabilizing solution | unit: g |
|---|---|
| Formalin (37%) | 2.0 ml |
| Polyoxyethylene p-monononylphenyl ether (average degree of polymerization: 10) | 0.3 |
| Disodium ethylenediaminetetraacetate | 0.05 |
| Add water | To make 1.0 l |
| pH | 5.0 to 8.0 |

To examine the dye image preservability of the thus-processed samples, the samples were irradiated with a xenon light source (180,000 lux) for 24 hours to prepare the samples. Fastness to light was evaluated. The results are shown in Table 1.

TABLE 1

| Sample No. | Coupler | Fastness to light* |
|---|---|---|
| 101 | ExY-11 (Comp. Ex.) | 1.72 |
| 102 | (1) (Invention) | 1.94 |
| 103 | (2) (Invention) | 1.96 |
| 104 | (3) (Invention) | 1.97 |
| 105 | (10) (Invention) | 1.96 |
| 106 | (12) (Invention) | 1.92 |
| 107 | (13) (Invention) | 1.88 |
| 108 | (20) (Invention) | 1.97 |
| 109 | (21) (Invention) | 1.95 |

*Density after irradiated with xenon light for 24 hours at a yellow density of 2.0.

It is clear from the above results that the samples obtained by using the couplers of the present invention have a high image fastness to light.

EXAMPLE 2

A cellulose triacetate film support having a subbing applied thereto was coated with the following layers having the following compositions to prepare a multilayer color photographic material as sample 201.

Compositions of sensitive layers

Numerals show the coating weights of ingredients represented by g/m². The amount of the silver halides are represented by coating weights in terms of silver. The amount of each sensitizing dye is represented by coating weight by mol per mol of silver halide in the same layer.

| Sample 201 | |
|---|---|
| First Layer (antihalation layer) | |
| Black colloidal silver | 0.18 (as silver) |
| Gelatin | 1.40 |
| Second Layer (interlayer) | |
| 2,5-Di-t-pentadecylhydroquinone | 0.18 |
| EX-1 | 0.07 |
| EX-3 | 0.02 |
| EX-12 | 0.002 |
| U-1 | 0.06 |
| U-2 | 0.08 |
| U-3 | 0.10 |
| HBS-1 | 0.10 |
| HBS-2 | 0.02 |
| Gelatin | 1.04 |
| Third Layer (first red-sensitive emulsion layer) | |
| Emulsion A | 0.25 (as silver) |
| Emulsion B | 0.25 (as silver) |
| Sensitizing dye I | $6.9 \times 10^{-5}$ |
| Sensitizing dye II | $1.8 \times 10^{-5}$ |
| Sensitizing dye III | $3.1 \times 10^{-4}$ |
| EX-2 | 0.335 |
| EX-10 | 0.020 |
| U-1 | 0.07 |
| U-2 | 0.05 |
| U-3 | 0.07 |
| HBS-1 | 0.060 |
| Gelatin | 0.87 |
| Fourth Layer (second red-sensitive emulsion layer) | |
| Emulsion C | 1.0 (as silver) |
| Sensitizing dye I | $5.1 \times 10^{-5}$ |
| Sensitizing dye II | $1.4 \times 10^{-5}$ |
| Sensitizing dye III | $2.3 \times 10^{-4}$ |
| EX-2 | 0.400 |
| EX-3 | 0.050 |
| EX-10 | 0.015 |
| U-1 | 0.07 |
| U-2 | 0.05 |
| U-3 | 0.07 |
| Gelatin | 1.30 |
| Fifth Layer (third red-sensitive emulsion layer) | |
| Emulsion D | 1.60 (as silver) |
| Sensitizing dye I | $5.4 \times 10^{-5}$ |
| Sensitizing dye II | $1.4 \times 10^{-5}$ |
| Sensitizing dye III | $2.4 \times 10^{-4}$ |
| EX-3 | 0.010 |
| EX-4 | 0.080 |
| EX-2 | 0.097 |
| HBS-1 | 0.22 |
| HBS-2 | 0.10 |
| Gelatin | 1.63 |
| Sixth Layer (interlayer) | |
| EX-5 | 0.040 |
| HBS-1 | 0.020 |
| Gelatin | 0.80 |
| Seventh Layer (first green-sensitive emulsion layer) | |
| Emulsion A | 0.15 (as silver) |
| Emulsion B | 0.15 (as silver) |
| Sensitizing dye V | $3.0 \times 10^{-5}$ |
| Sensitizing dye VI | $1.0 \times 10^{-4}$ |
| Sensitizing dye VII | $3.8 \times 10^{-4}$ |
| EX-6 | 0.260 |
| EX-1 | 0.021 |
| EX-7 | 0.030 |
| EX-8 | 0.025 |
| HBS-1 | 0.100 |
| HBS-3 | 0.010 |
| Gelatin | 0.63 |
| Eighth Layer (Second green-sensitive emulsion layer) | |
| Emulsion C | 0.45 (as silver) |
| Sensitizing dye V | $2.1 \times 10^{-5}$ |
| Sensitizing dye VI | $7.0 \times 10^{-5}$ |
| Sensitizing dye VII | $2.6 \times 10^{-4}$ |

-continued

Sample 201

| | |
|---|---|
| EX-6 | 0.094 |
| EX-8 | 0.018 |
| EX-7 | 0.026 |
| HBS-1 | 0.160 |
| HBS-3 | 0.008 |
| Gelatin | 0.50 |
| Ninth Layer (third green-sensitive emulsion layer) | |
| Emulsion E | 1.2 |
| | (as silver) |
| Sensitizing dye V | $3.5 \times 10^{-5}$ |
| Sensitizing dye VI | $8.0 \times 10^{-5}$ |
| Sensitizing dye VII | $3.0 \times 10^{-4}$ |
| EX-13 | 0.015 |
| EX-11 | 0.100 |
| EX-1 | 0.025 |
| HBS-1 | 0.25 |
| HBS-2 | 0.10 |
| Gelatin | 1.54 |
| Tenth Layer (yellow filter layer) | |
| Yellow colloidal silver | 0.05 |
| | (as silver) |
| EX-5 | 0.08 |
| HBS-1 | 0.03 |
| Gelatin | 0.95 |
| Eleventh Layer (first blue-sensitive emulsion layer) | |
| Emulsion A | 0.08 |
| | (as silver) |
| Emulsion B | 0.07 |
| | (as silver) |
| Emulsion F | 0.07 |
| | (as silver) |
| Sensitizing dye VIII | $3.5 \times 10^{-4}$ |
| EX-9 | 0.361 |
| EX-8 | 0.042 |

-continued

Sample 201

| | |
|---|---|
| HBS-1 | 0.28 |
| Gelatin | 1.10 |
| Twelfth Layer (second blue-sensitive emulsion layer) | |
| Emulsion G | 0.45 |
| | (as silver) |
| Sensitizing dye VIII | $2.1 \times 10^{-4}$ |
| EX-9 | 0.077 |
| EX-10 | 0.007 |
| HBS-1 | 0.05 |
| Gelatin | 0.78 |
| Thirteenth Layer (third blue-sensitive emulsion layer) | |
| Emulsion H | 0.77 |
| | (as silver) |
| Sensitizing dye VIII | $2.2 \times 10^{-4}$ |
| EX-9 | 0.10 |
| HBS-1 | 0.07 |
| Gelatin | 0.69 |
| Fourteenth Layer (first protective layer) | |
| Emulsion I | 0.20 |
| | (as silver) |
| U-4 | 0.11 |
| U-5 | 0.17 |
| HBS-1 | 0.05 |
| Gelatin | 1.00 |
| Fifteenth Layer (second protective layer) | |
| Polymethyl acrylate particles | 0.54 |
| (diameter: about 1.5 μm) | |
| S-1 | 0.20 |
| Gelatin | 1.20 |

In addition to the above-described ingredients, hardening agent H-1 for gelatin and surfactants were added to each layer.

Emulsion Characteristics

| | Average AgI content (%) | Mean grain size (μm) | Coefficient of variation in grain size (%) | Diameter/ thickness ratio | Ratio of amount of silver (AgI content, %) |
|---|---|---|---|---|---|
| Emulsion A | 4.0 | 0.45 | 27 | 1 | core/shell = ⅓ (13/1), double structure grain |
| Emulsion B | 8.9 | 0.70 | 14 | 1 | core/shell = 3/7 (25/2), double structure grain |
| Emulsion C | 10 | 0.75 | 30 | 2 | core/shell = ½ (24/3), double structure grain |
| Emulsion D | 16 | 1.05 | 35 | 2 | core/shell = 4/6 (40/0), double structure grain |
| Emulsion E | 10 | 1.05 | 35 | 3 | core/shell = ½ (24/3), double structure grain |
| Emulsion F | 4.0 | 0.25 | 28 | 1 | core/shell = ⅓ (13/1), double structure grain |
| Emulsion G | 14.0 | 0.75 | 25 | 2 | core/shell = ½ (42/0), double structure grain |
| Emulsion H | 14.5 | 1.30 | 25 | 3 | core/shell = 37/63 (34/3), double structure grain |
| Emulsion I | 1 | 0.07 | 15 | 1 | uniform grain |

EX-1

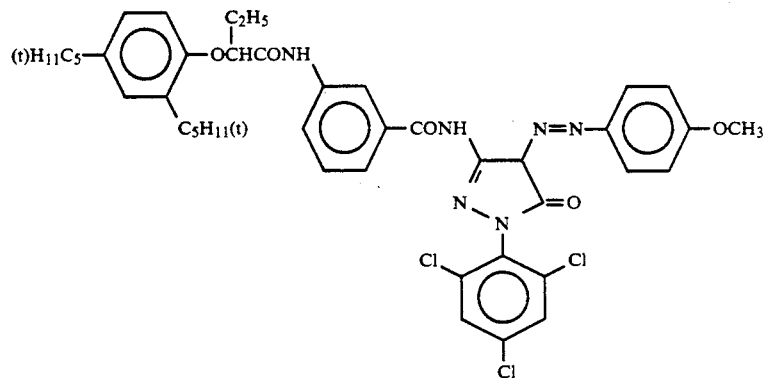

EX-2

-continued
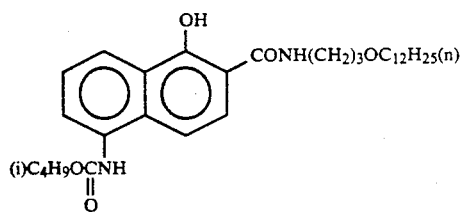
EX-3
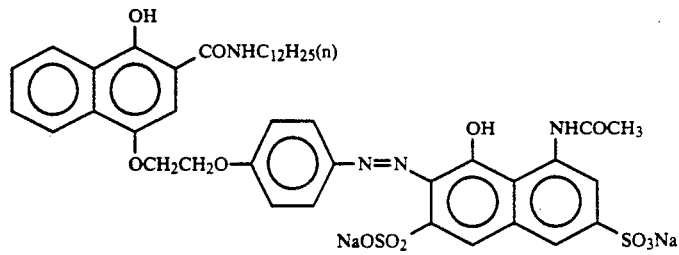
EX-4
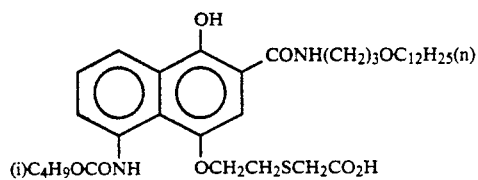
EX-5
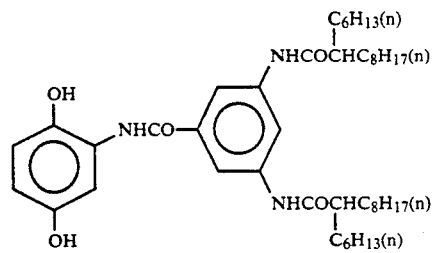
EX-6
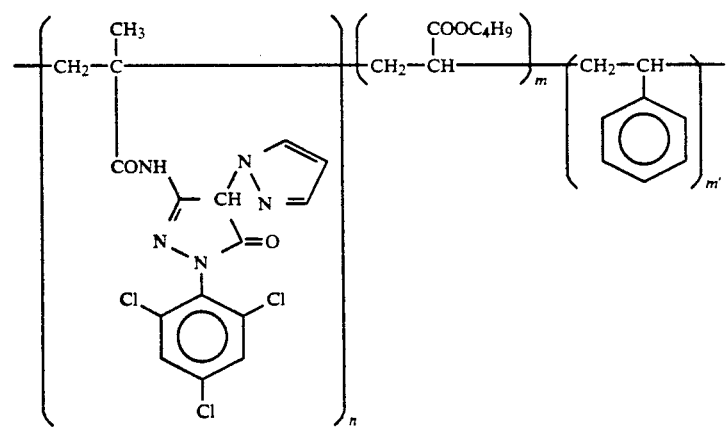
n = 50
m = 25
m' = 25
mol. wt. about 20,000
EX-7

EX-8
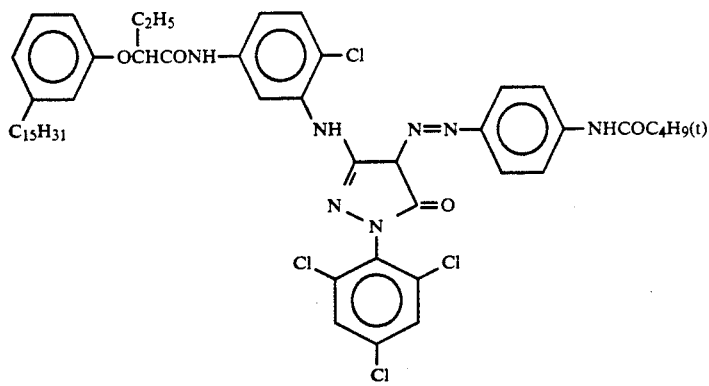
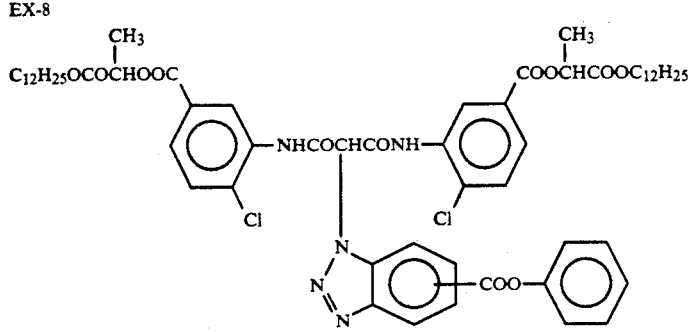
EX-9
(coupler described in JP-A-1-207749)
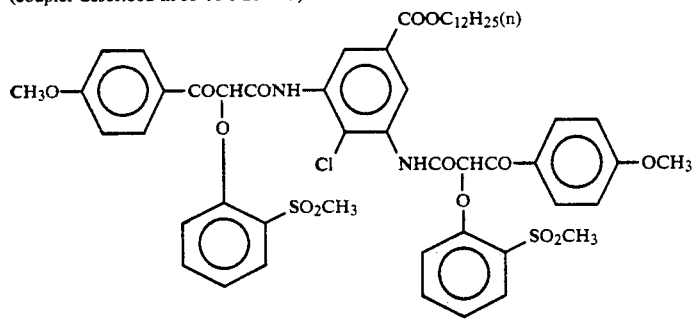
EX-10
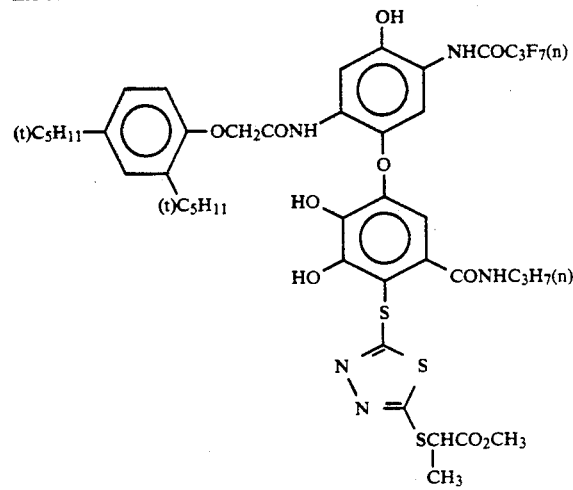
EX-11

-continued
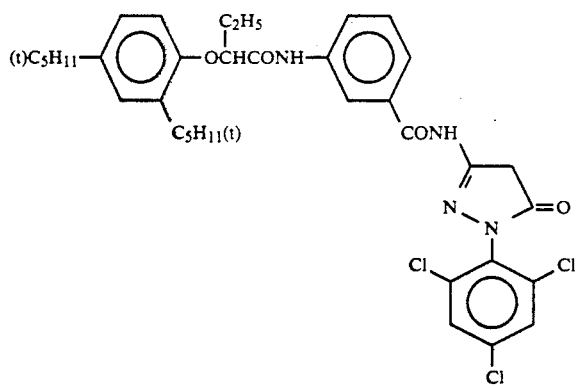
EX-12
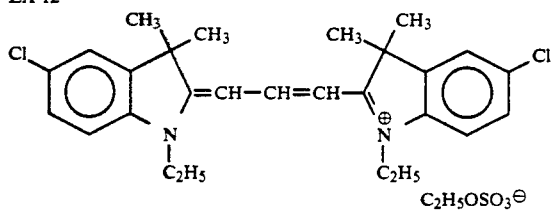
EX-13
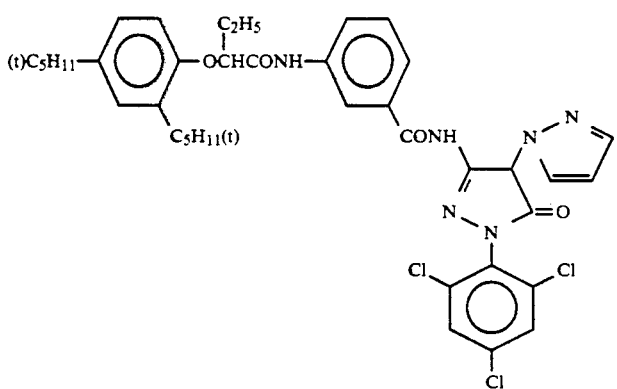
U-1
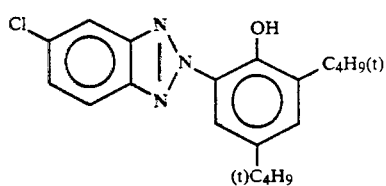
U-2
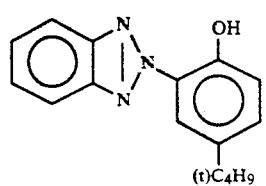
U-3
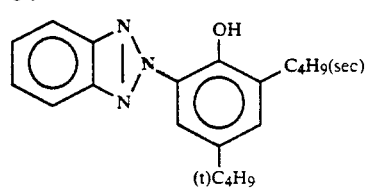

U-4
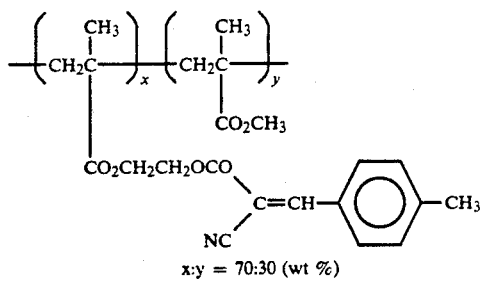
x:y = 70:30 (wt %)
U-5
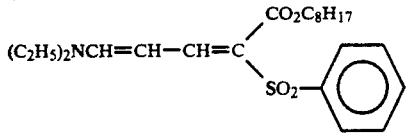
HBS-1
Tricresyl phosphate
HBS-2
Di-n-butyl phthalate
HBS-3
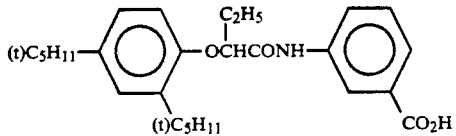
Sensitizing dye I
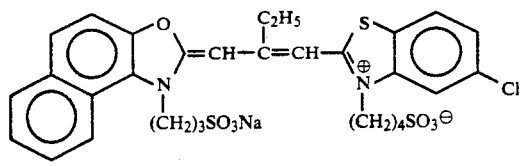
Sensitizing dye II
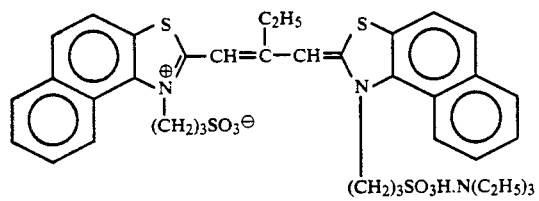
Sensitizing dye III
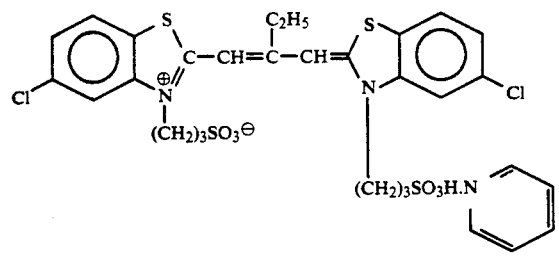
Sensitizing dye V
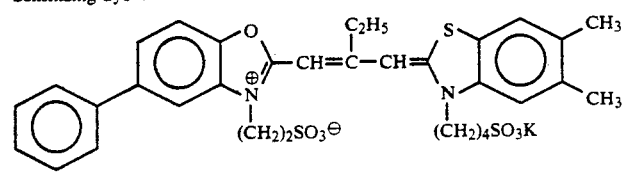

Sensitizing dye VI

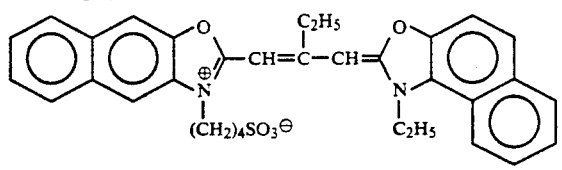

Sensitizing dye VII

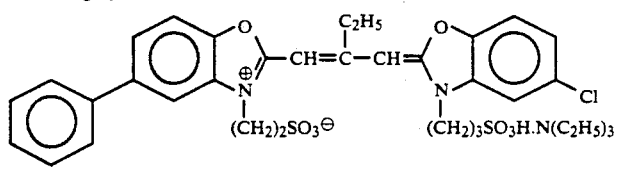

Sensitizing dye VIII

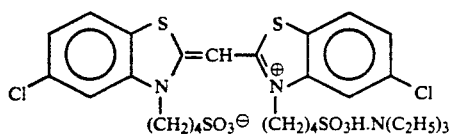

S-1

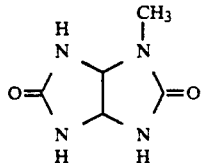

H-1

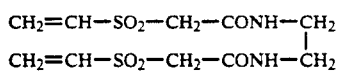

Preparation of Samples 202 to 204

Samples 202 to 204 were prepared in the same way as in the preparation of sample 201 except that an equimolar amount of each coupler indicated in Table 2 was added to the eleventh layer, the twelfth layer and the thirteenth layer in place of Ex-9. Each of the samples 201 to 204 was cut into a piece 35 mm in width, exposed through a wedge and subjected to the following processing stages.

| | Processing Method | | | |
|---|---|---|---|---|
| Stages | Processing Time | Processing Temp. | Replenishment Rate | Tank Capacity |
| Color development | 2 min. 30 sec | 40° C. | 10 ml | 8 l |
| Bleach-fix | 3 min. 00 sec | 40° C. | 20 ml | 8 l |
| Rinse (1) | 20 sec | 35° C. | Countercurrent System from (2) to (1) | 2 l |
| Rinse (2) | 20 sec | 35° C. | 10 ml | 2 l |
| Stabilization | 20 sec | 35° C. | 10 ml | 2 l |
| Drying | 50 sec | 65° C. | | |

Replenishment rate being per 35 mm wide × 1 m long.
Each processing solution had the following composition.

| Color Developing Solution | Mother Solution | Replenisher |
|---|---|---|
| Diethylenetriaminepentaacetic acid | 2.0 g | 2.0 g |
| 1-Hydroxyethylidene-1,1-diphosphonic acid | 3.0 g | 3.2 g |
| Sodium sulfite | 4.0 g | 5.5 g |
| Potassium carbonate | 30.0 g | 45.0 g |
| Potassium bromide | 1.4 g | — |
| Potassium iodide | 1.5 mg | — |
| Hydroxyamine sulfate | 2.4 g | 3.0 g |
| 4-[N-Ethyl-N-(β-hydroxyethyl) amino]-2-methylaniline sulfate | 4.5 g | 7.5 g |
| Add water to make | 1.0 l | 1.0 l |
| pH | 10.05 | 10.20 |
| Bleach-fix Solution (Mother solution and replenisher being the same) | | |
| Ethylenediaminetetraacetic acid iron(III) ammonium | 50.0 g | |
| Disodium ethylenediaminetetraacetate | 5.0 g | |
| Sodium sulfite | 12.0 g | |
| Aqueous solution of ammonium thiosulfate (70%) | 260.0 ml | |
| Acetic acid (98%) | 5.0 ml | |
| Bleaching accelerator | 0.01 mol | |

$$\left[\begin{array}{c} N \longrightarrow \\ | \\ N \diagdown \\ \diagup NH \\ SH \end{array}\right]$$

| Add water to make | 1.0 liter |

| | |
|---|---|
| -continued | |
| pH | 6.0 |

Rinsing Solution

Mother solution and replenisher being the same

Tap water was passed through a mixed bed column packed with an H type strongly acidic cation exchange resin (Amberlite IR-120B, a product of Rohm & Haas Co.) and an OH type anion exchange resin (Amberlite IR-400) to thereby reduce the concentration of each of the calcium and magnesium ions to no higher than 3 mg/l. Sodium isocyanurate dichloride (20 mg/l) and sodium sulfate (1.5 g/l) were added thereto. The pH of the solution was in the range of 6.5 to 7.5.

| Stabilizing Solution (Mother solution and replenisher being the same) | |
|---|---|
| Formalin (37%) | 2.0 ml |
| Polyoxyethylene p-mononoylphenyl ether (average degree of polymerization: 10) | 0.3 g |
| Disodium ethylenediaminetetraacetate | 0.05 g |
| Add water to make | 1.0 liter |
| pH | 5.0-8.0 |

To examine the dye image preservability of the resulting processed samples, the samples were irradiated with a xenon light source (180,000 lux) to prepare the samples. Fastness to light was evaluated. The results are shown in Table 2.

TABLE 2

| Sample No. | Coupler | | Fastness to Light* |
|---|---|---|---|
| 201 | Ex-9 | (Comp. Ex.) | 1.68 |
| 202 | (51) | (Invention) | 1.91 |
| 203 | (52) | (Invention) | 1.93 |
| 204 | (53) | (Invention) | 1.88 |

*Density after irradiated with xenon light for 24 hours at a yellow density of 2.0.

It is clear from the above results that dye images obtained by using the couplers of the present invention have high fastness to light in comparison with a known bis-type coupler (Ex-9).

EXAMPLE 3

Both sides of a paper support were laminated with polyethylene. The surface of the resulting support was coated with the following layers to prepare a multilayer color photographic paper having the following layer structure. Coating solutions were prepared in the following manner.

Preparation of Coating Solution for First Layer 19.7 g of yellow coupler (the coupler of the present invention), 4.4 g of dye image stabilizer (Cpd-1) and 0.7 g of dye image stabilizer (Cpd-7) were added to 27.2 cc of ethyl acetate and 8.2 g of solvent (Solv-1) to dissolve them. The resulting solution was emulsified and dispersed in 185 cc of a 10% aqueous gelatin solution containing 8 cc of 10% sodium dodecylbenzenesulfonate. Separately, there was prepared a sulfur-sensitized silver chlorobromide emulsion (cube, a 3:7 (by molar ratio in terms of silver) mixture of an emulsion (average grain size: 0.88 μm) and an emulsion (average grain size: 0.70 μm), coefficient of variation in grain size distribution, 0.08 and 0.10, respectively, 0.2 mol% of silver bromide being localized on the surface of grain in each emulsion) by adding $2.0 \times 10^{-4}$ mol (per mol of silver) of each of the following blue-sensitive sensitizing dyes to the larger size emulsion and $2.5 \times 10^{-4}$ mol (per mol of silver) of each of the following blue-sensitive sensitizing dyes to the smaller size emulsion and then carrying out sulfur sensitization. This emulsion and the above emulsified emulsion were mixed and dissolved. A coating solution for the first layer was prepared so as to give the following composition. Coating solutions for the second layer to the seventh layer were prepared in the same manner as in the coating solution for the first layer. Sodium salt of 1-oxy-3,5-dichloro-s-triazine was used as the hardening agent for gelatin in each layer.

The following spectral sensitizing dyes were used for the following layers.

Blue-sensitive Emulsion Layer:

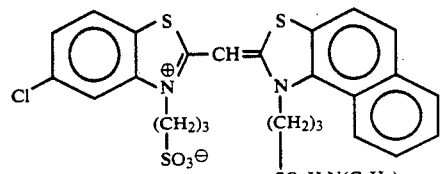

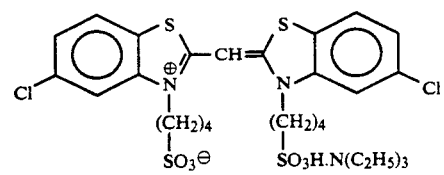

($2.0 \times 10^{-4}$ mol (per mol of silver halide) of each of the dyes being added to the larger size emulsion, and $2.5 \times 10^{-4}$ mol (per mol of silver halide) of each of the dyes being added to the smaller size emulsion).

Green-sensitive Emulsion Layer:

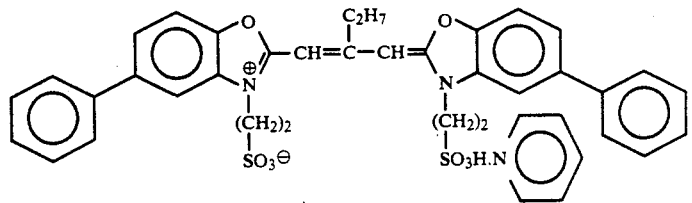

($4.0 \times 10^{-4}$ mol per mol of silver halide being added to the larger size emulsion and $5.6 \times 10^{-4}$ mol per mol of silver halide being added to the smaller size emulsion), and

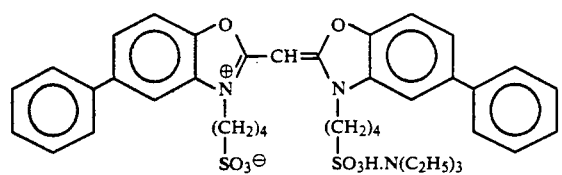

($7.0 \times 10^{-5}$ mol per mol of silver halide being added to the larger size emulsion and $1.0 \times 10^{-5}$ mol per mol of silver halide being added to the smaller size emulsion).

Red-Sensitive Emulsion Layer:

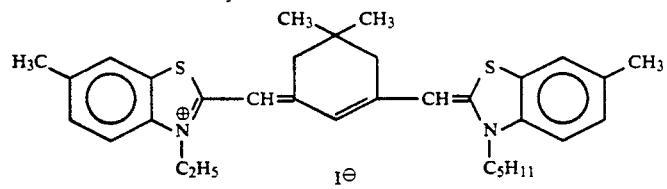

($0.9 \times 10^{-4}$ mol being added to the larger size emulsion and $1.1 \times 10^{-4}$ mol being added to the smaller size emulsion, each amount being per mol of silver halide).

$2.6 \times 10^{-3}$ mol of the following compound per mol of silver halide was added to the red-sensitive emulsion layer.

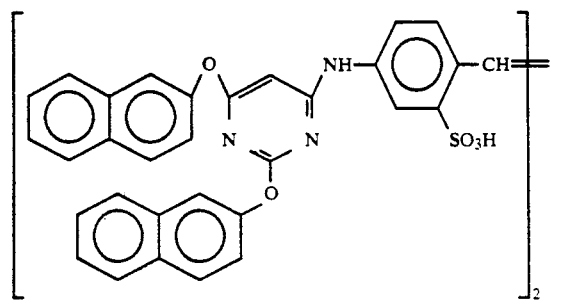

$8.5 \times 10^{-5}$ mol, $7.7 \times 10^{-4}$ mol and $2.5 \times 10^{-4}$ mol of 1-(5-methylureidophenyl-5-mercaptotetrazole per mol of silver halide were added to the blue-sensitive emulsion layer, green-sensitive emulsion layer and red-sensitive emulsion layer, respectively.

$1 \times 10^{-4}$ mol and $2 \times 10^{-4}$ mol of 4-hydroxy-6-methyl-1,3,3a,7-tetraazaindene per mole of silver halide were added to the blue-sensitive emulsion layer and the green-sensitive emulsion layer, respectively.

The following dyes were added to emulsion layers to prevent irradiation:

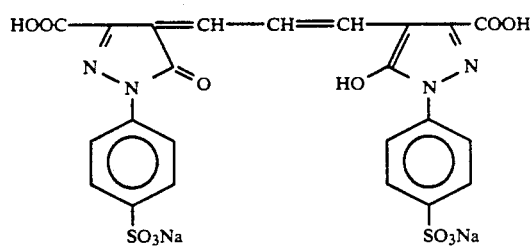

and

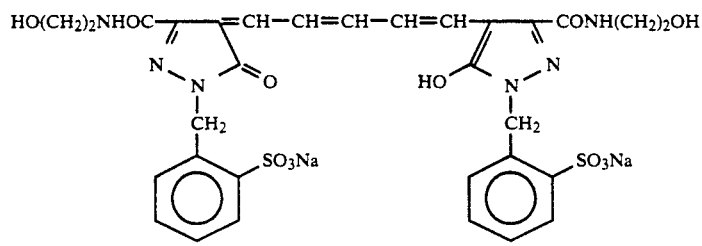

Layer Structure

Each layer had the following composition. Numerals represent coating weight (g/m$^2$). The amounts of silver halide emulsions are represented by coating weight in terms of silver.

Support

Polyethylene-laminated paper (Polyethylene on the side of the first layer contains white pigment (TiO$_2$) and bluish dye (ultramarine)

| | |
|---|---|
| First Layer: Blue-sensitive Layer | |
| The above silver chlorobromide emulsion | 0.30 |
| Gelatin | 1.86 |
| Yellow coupler (coupler (14) of invention) | 0.82 |
| Dye image stabilizer (Cpd-1) | 0.19 |
| Solvent (Solv-1) | 0.35 |
| Dye image stabilizer (Cpd-7) | 0.06 |
| Second Layer: Color Mixing Inhibiting Layer | |
| Gelatin | 0.99 |
| Color mixing inhibitor (Cpd-5) | 0.08 |
| Solvent (Solv-1) | 0.16 |
| Solvent (Solv-4) | 0.08 |
| Third Layer: Green-sensitive Layer | |
| Silver chlorobromide emulsion (cube, a 1:3 (by Ag molar ratio) mixture of an emulsion having a mean grain size of 0.55 μm and an emulsion having a mean grain size of 0.39 μm, a coefficient of variation in grain size distribution: 0.10 and 0.08, respectively, 0.8 mol % of AgBr being localized on the surface of grain in each layer) | 0.12 (as silver) |
| Gelatin | 1.24 |
| Magenta coupler (ExM) | 0.20 |
| Dye image stabilizer (Cpd-2) | 0.03 |
| Dye image stabilizer (Cpd-3) | 0.15 |
| Dye image stabilizer (Cpd-4) | 0.02 |
| Dye image stabilizer (Cpd-9) | 0.02 |
| Solvent (Solv-2) | 0.40 |
| Fourth Layer: Ultraviolet Light Absorbing Layer | |
| Gelatin | 1.58 |
| Ultraviolet light absorber (UV-1) | 0.47 |
| Color mixing inhibitor (Cpd-5) | 0.05 |
| Solvent (Solv-5) | 0.24 |
| Fifth Layer: Red-sensitive Layer | |
| Silver chlorobromide emulsion (cube, a 1:4 (by Ag molar ratio) mixture of an emuslion having a mean grain size of 0.58 μm and an emulsion having a mean grain size of 0.45 μm, a coefficient of variation in grain size distribution: 0.09 and 0.11, respectively, 0.6 mol % of AgBr being localized on the surface of grain in each emulsion) | 0.23 (as silver) |
| Gelatin | 1.34 |
| Cyan coupler (ExC) | 0.32 |
| Dye image stabilizer (Cpd-6) | 0.17 |
| Dye image stabilizer (Cpd-7) | 0.40 |
| Dye image stabilizer (Cpd-8) | 0.04 |
| Solvent (Solv-6) | 0.15 |
| Sixth Layer: Ultraviolet Light Absorbing Layer | |
| Gelatin | 0.53 |
| Ultraviolet Light Absorber (UV-1) | 0.16 |
| Color mixing inhibitor (Cpd-5) | 0.02 |
| Solvent (Solv-5) | 0.08 |
| Seventh Layer: Protective Layer | |
| Gelatin | 1.33 |
| Acrylic-modified copolymer of polyvinyl alcohol (degree of modification: 17%) | 0.17 |
| Liquid paraffin | 0.03 |

(ExM) Magenta coupler

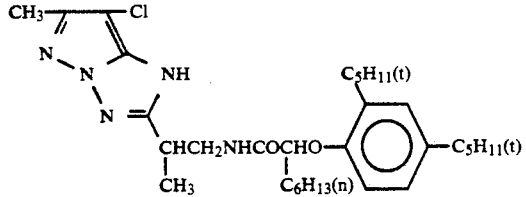

and

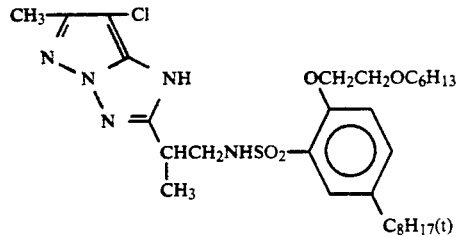

(ExC) Cyan coupler

-continued
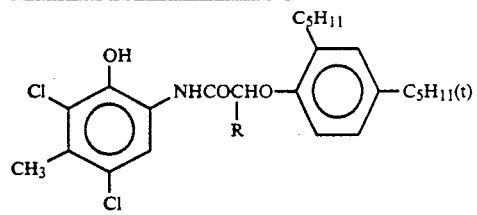
R: C$_2$H$_5$ and C$_4$H$_9$
and
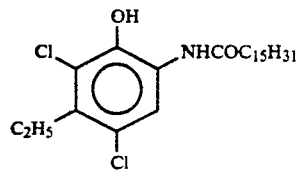
2:4:4 (by weight) mixture
(Cpd-1) Dye image stabilizer
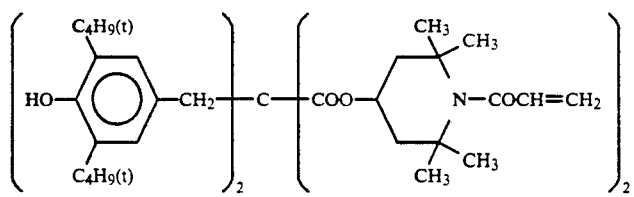
(Cpd-2) Dye image stabilizer
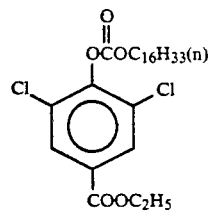
(Cpd-3) Dye image stabilizer
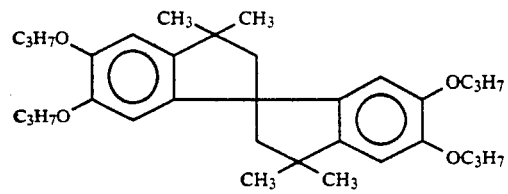
(Cpd-4) Dye image stabilizer
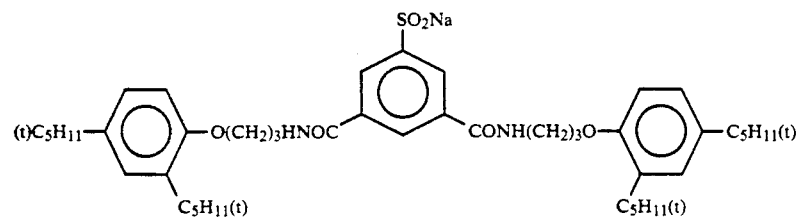
(Cpd-5) Color mixing inhibitor

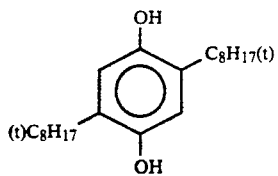
(Cpd-6) Dye image stabilizer
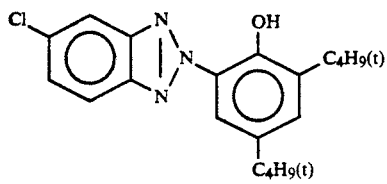
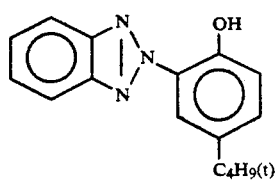
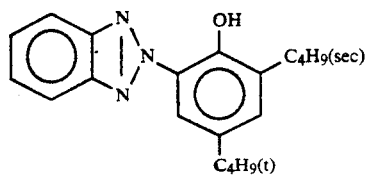
2:4:4 mixture (by weight)
(Cpd-7) Dye image stabilizer
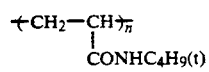
(Average MW 60,000)
(Cpd-8) Dye image stabilizer
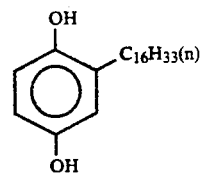
(Cpd-9) Dye image stabilizer
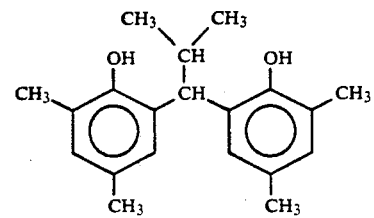
(UV-1) Ultraviolet light absorber

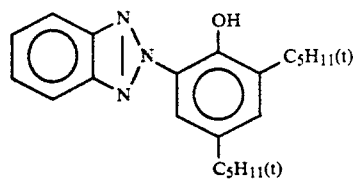
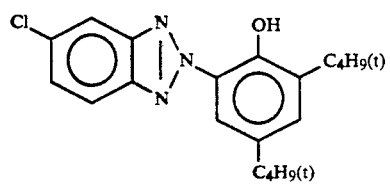
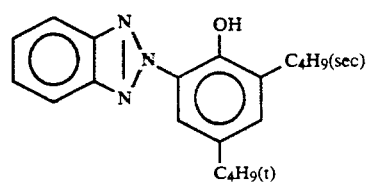
4:2:4 mixture (by weight)
(Solv-1) Solvent
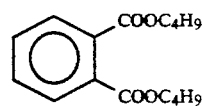
(Solv-2) Solvent
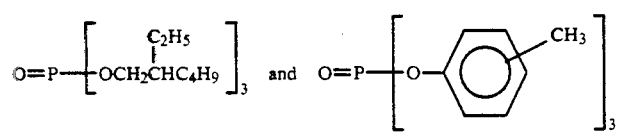
2:1 mixture (by volume)
(Solv-4) Solvent
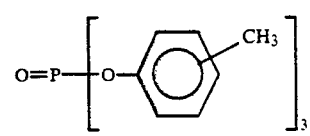
(Solv-5) Solvent
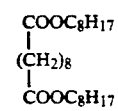
(Solv-6) Solvent
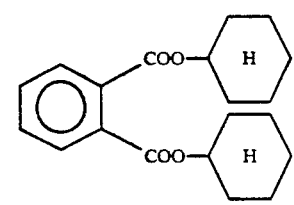

The above photographic material was exposed through a wedge and processed in the following stages.

| Processing Stage | Temperature | Time |
|---|---|---|
| Color development | 35° C. | 45 sec |
| Bleach-fix | 30–35° C. | 45 sec |
| Rinse (1) | 30–35° C. | 20 sec |
| Rinse (2) | 30–35° C. | 20 sec |
| Rinse (3) | 30–35° C. | 20 sec |
| Rinse (4) | 30–35° C. | 30 sec |
| Drying | 70–80° C. | 60 sec |

A four tank countercurrent system of rinse (4) to (1) was used.

Each processing solution had the following composition.

| Color Developing Solution | |
|---|---|
| Water | 800 ml |
| Ethylenediamine-N,N,N',N'-tetra-methylenephosphonic acid | 1.5 g |
| Triethanolamine | 8.0 g |
| Sodium chloride | 1.4 g |
| Potassium carbonate | 25 g |
| N-ethyl-N-(β-methanesulfonamidoethyl)-3-methyl-4-aminoaniline sulfate | 5.0 g |
| N,N-Bis(carboxymethyl)hydrazine | 7.0 g |
| Fluorescent brightener (WHITEX 4B, a product of Sumitomo Chemical Co., Ltd.) | 1.0 g |
| Add water to make | 1000 ml |
| pH (25° C.) | 10.10 |
| Bleach-fix Solution | |
| Water | 400 ml |
| Ammonium thiosulfate (70%) | 100 ml |
| Sodium sulfite | 18 g |
| Ethylenediaminetetraacetic acid iron(III) ammonium | 55 g |
| Disodium ethylenediaminetetraacetate | 3 g |
| Ammonium bromide | 40 g |
| Glacial acetic acid | 8 g |
| Add water to make | 1000 ml |
| pH (25° C.) | 5.5 |

Rinsing Solution

Ion-exchanged water (concentration of each of calcium and magnesium ions being no higher than 3 ppm).

The resulting processed sample gave a dye image having sufficiently high fastness to light.

EXAMPLE 4

Preparation of Sample 401

A cellulose triacetate film support having a thickness of 127 μm and an undercoat applied thereto was coated with the following layers having the following compositions to prepare a multi-layer color photographic material as sample 401. Numerals represent amounts added per m². The effects of compounds added are not limited tot he designated use.

| First Layer: Antihalation Layer | |
|---|---|
| Black colloidal silver | 0.25 g |
| Gelatin | 1.9 g |
| Ultraviolet light absorber U-1 | 0.04 g |
| Ultraviolet light absorber U-2 | 0.1 g |
| Ultraviolet light absorber U-3 | 0.1 g |
| Ultraviolet light absorber U-4 | 0.1 g |
| Ultraviolet light absorber U-6 | 0.1 g |
| High-boiling organic solvent Oil-1 | 0.1 g |
| Second Layer: Interlayer | |
| Gelatin | 0.40 g |
| Compound Cpd-D | 10 mg |
| High-boiling organic solvent Oil-3 | 0.1 g |
| Dye D-4 | 0.4 mg |
| Third Layer: Interlayer | |
| Finely divided silver iodobromide emulsion (surface and interior being fogged; mean grain size: 0.06 μm, coefficient of variation: 18%, AgI content: 1 mol %) | 0.05 g (as silver) |
| Gelatin | 0.4 g |
| Fourth Layer: Low-sensitivity Red-sensitive Emulsion Layer | |
| Emulsion A | 0.2 g (as silver) |
| Emulsion B | 0.3 g (as silver) |
| Gelatin | 0.8 g |
| Coupler C-1 | 0.15 g |
| Coupler C-2 | 0.05 g |
| Coupler C-9 | 0.05 g |
| Compound Cpd-D | 10 mg |
| High-boiling organic solvent Oil-2 | 0.1 g |
| Fifth Layer: Medium-sensitivity red-sensitive Emulsion Layer | |
| Emulsion B | 0.2 g (as silver) |
| Emulsion C | 0.3 g (as silver) |
| Gelatin | 0.8 g |
| Coupler C-1 | 0.2 g |
| Coupler C-2 | 0.05 g |
| Coupler C-3 | 0.2 g |
| High-boiling organic solvent Oil-2 | 0.1 g |
| Sixth Layer: High-sensitivity red-sensitive Emulsion Layer | |
| Emulsion D | 0.4 g (as silver) |
| Gelatin | 1.1 g |
| Coupler C-1 | 0.3 g |
| Coupler C-3 | 0.7 g |
| Additive P-1 | 0.1 g |
| Seventh Layer: Interlayer | |
| Gelatin | 0.6 g |
| Additive M-1 | 0.3 g |
| Color mixing inhibitor Cpd-K | 2.6 mg |
| Ultraviolet light absorber U-1 | 0.1 g |
| Ultraviolet light absorber U-6 | 0.1 g |
| Dye D-1 | 0.02 g |
| Eighth Layer: Interlayer | |
| Silver iodobromide emulsion (surface and interior being fogged; mean grain size: 0.06 μm, coefficient of variation: 16%, AgI content: 0.3 mol %) | 0.02 g (as silver) |
| Gelatin | 1.0 g |
| Additive P-1 | 0.2 g |
| Color mixing inhibitor Cpd-J | 0.1 g |
| Color mixing inhibitor Cpd-A | 0.1 g |
| Ninth Layer: Low-sensitivity Green-sensitive Emulsion Layer | |
| Emulsion E | 0.3 g (as silver) |
| Emulsion F | 0.1 g (as silver) |
| Emulsion G | 0.1 g (as silver) |
| Gelatin | 0.5 g |
| Coupler C-7 | 0.05 g |
| Coupler C-8 | 0.20 g |
| Compound Cpd-B | 0.03 g |
| Compound Cpd-D | 10 mg |
| Compound Cpd-E | 0.02 g |
| Compound Cpd-F | 0.02 g |
| Compound Cpd-G | 0.02 g |
| Compound Cpd-H | 0.02 g |
| High-boiling organic solvent Oil-1 | 0.1 g |
| High-boiling organic solvent Oil-2 | 0.1 g |
| Tenth Layer: Medium-sensitivity Green-sensitive Emulsion Layer | |
| Emulsion G | 0.3 g (as silver) |
| Emulsion H | 0.1 g (as silver) |

|  |  |
|---|---|
| Gelatin | 0.6 g |
| Coupler C-7 | 0.2 g |
| Coupler C-8 | 0.1 g |
| Compound Cpd-B | 0.03 g |
| Compound Cpd-E | 0.02 g |
| Compound Cpd-F | 0.02 g |
| Compound Cpd-G | 0.05 g |
| Compound Cpd-H | 0.05 g |
| High-boiling organic solvent Oil-2 | 0.01 g |
| Eleventh Layer: High-sensitivity Green-sensitive Emulsion Layer | |
| Emulsion I | 0.5 g |
|  | (as silver) |
| Gelatin | 1.0 g |
| Coupler C-4 | 0.3 g |
| Coupler C-8 | 0.1 g |
| Compound Cpd-B | 0.08 g |
| Compound Cpd-E | 0.02 g |
| Compound Cpd-F | 0.02 g |
| Compound Cpd-G | 0.02 g |
| Compound Cpd H | 0.02 g |
| High-boiling organic solvent Oil-1 | 0.02 g |
| High-boiling organic solvent Oil-2 | 0.02 g |
| Twelfth Layer: Interlayer | |
| Gelatin | 0.6 g |
| Dye D-1 | 0.1 g |
| Dye D-2 | 0.05 |
| Dye D-3 | 0.07 |
| Thirteenth Layer: Yellow Filter Layer | |
| Yellow colloidal silver | 0.1 g |
|  | (as silver) |
| Gelatin | 1.1 g |
| Color mixing inhibitor Cpd-A | 0.01 g |
| High-boiling organic solvent Oil-1 | 0.01 g |
| Fourteenth Layer: Interlayer | |
| Gelatin | 0.6 g |
| Fifteenth Layer: Low-sensitivity Blue-sensitive Emulsion Layer | |
| Emulsion J | 0.4 g |
|  | (as silver) |
| Emulsion K | 0.1 g |
|  | (as silver) |
| Emulsion L | 0.1 g |
|  | (as silver) |
| Gelatin | 0.9 g |
| Coupler C-5 | 0.5 g |
| Sixteenth Layer: Medium-sensitivity Blue-sensitive Emulsion Layer | |
| Emulsion L | 0.1 g |
|  | (as silver) |
| Emulsion M | 0.4 g |
|  | (as silver) |
| Gelatin | 1.0 g |
| Coupler C-5 | 0.2 g |
| Coupler C-6 | 0.3 g |
| Seventeenth Layer: High-sensitivity Blue-sensitive Emulsion Layer | |
| Emulsion N | 0.4 g |
|  | (as silver) |
| Gelatin | 1.3 g |
| Coupler C-6 | 0.56 g |
| Eighteenth Layer: First Protective Layer | |
| Gelatin | 0.7 g |
| Ultraviolet light absorber U-1 | 0.04 g |
| Ultraviolet light absorber U-2 | 0.01 g |
| Ultraviolet light absorber U-3 | 0.03 g |
| Ultraviolet light absorber U-4 | 0.03 g |
| Ultraviolet light absorber U-5 | 0.05 g |
| Ultraviolet light absorber U-6 | 0.05 g |
| High-boiling organic solvent Oil-1 | 0.02 g |
| Formalin scavenger Cpd-C | 0.2 g |
| Formalin scavenger Cpd-I | 0.4 g |
| Dye D-3 | 0.05 g |
| Nineteenth Layer: Second Protective Layer | |
| Colloidal silver | 0.1 mg |
|  | (as silver) |
| Finely divided silver iodobromide emulsion (mean grain size: 0.06 μm, AgI content: 1 mol %) | 0.1 g (as silver) |
| Gelatin | 0.4 g |
| Twentieth Layer: Third Protective Layer | |
| Gelatin | 0.4 g |
| Polymethyl methacrylate (average particle size: 1.5 μm) | 0.1 g |
| Copolymer of methyl methacrylate and acrylic acid (4:6) (average particle size: 1.5 μm) | 0.1 g |
| Silicone oil | 0.03 g |
| Surfactant W-1 | 3.0 mg |
| Surfactant W-2 | 0.03 g |

In addition to the above-described ingredients, additives F-1 to F-8 were added to all emulsion layers. Further, hardening agent H-1 for gelatin, and surfactants W-3 and W-4 for coating and emulsification were added to each layer.

Furthermore, phenol, 1,2-benz-isothiazolin-3-one, 2-phenoxyethanol and phenethyl alcohol were added as an antiseptic and antifungal agent.

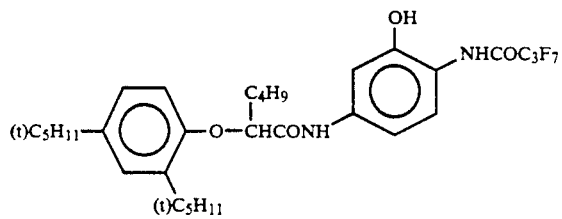

C-1

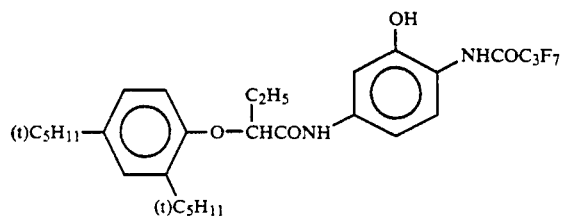

C-2

-continued
C-3
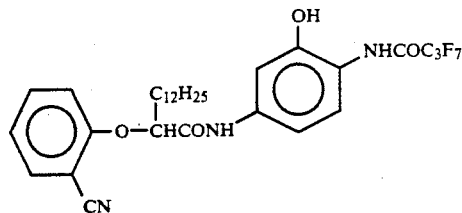
C-4
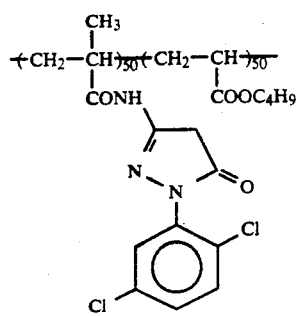
Numerals being wt %
Average MW about 25,000
(Conventional yellow coupler) C-5
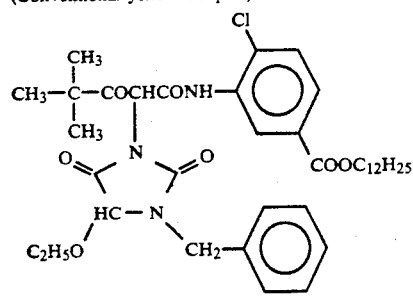
(Conventional yellow coupler) C-6
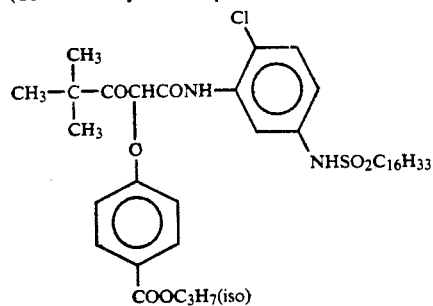
C-7
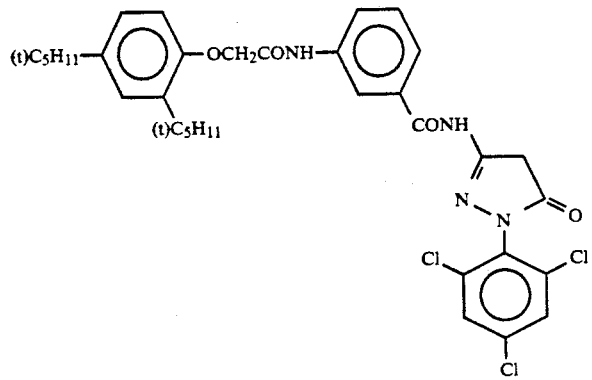

-continued
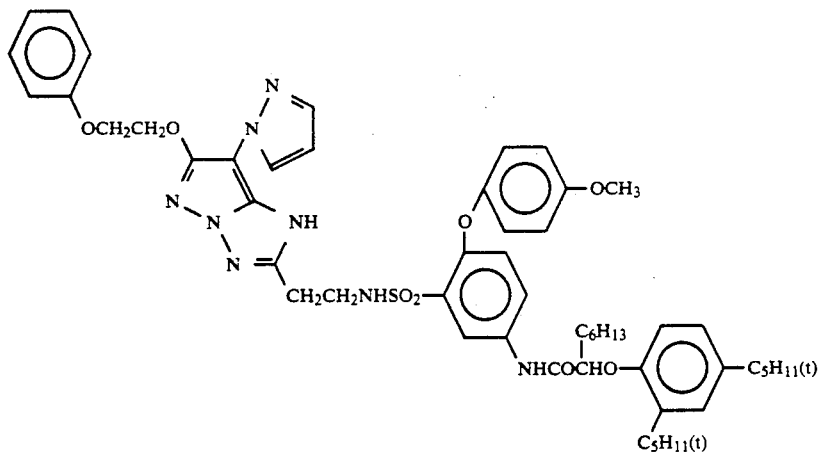
C-8
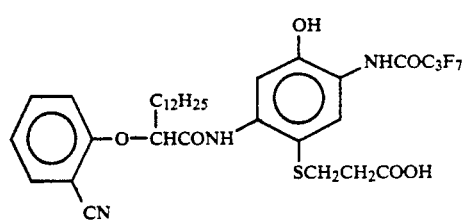
C-9
| | |
|---|---|
| Dibutyl phthalate | Oil-1 |
| Tricresyl phosphate | Oil-2 |
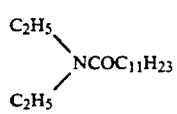
Oil-3
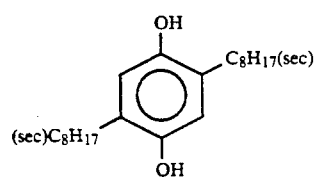
Cpd-A
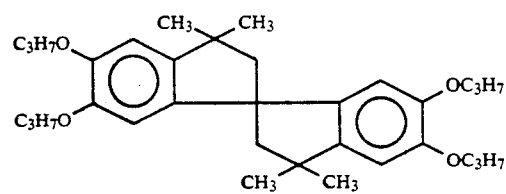
Cpd-B
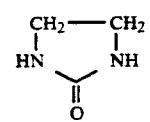
Cpd-C
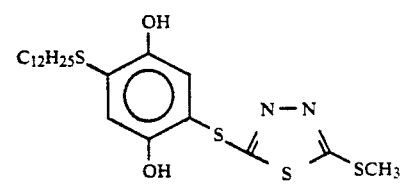
Cpd-D Cpd-E
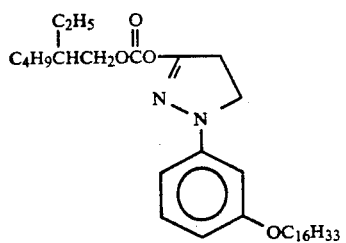
Cpd-F
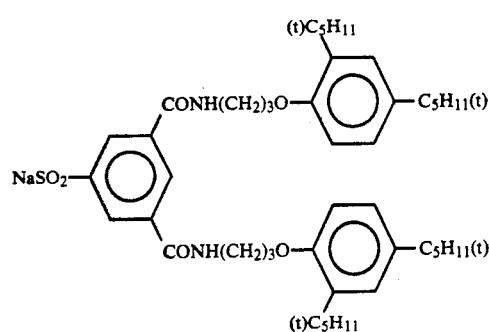
Cpd-G
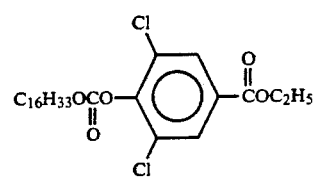
Cpd-H
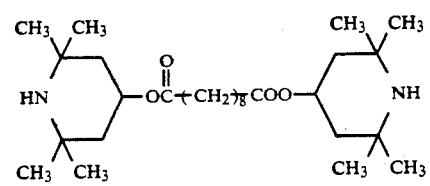
Cpd-I
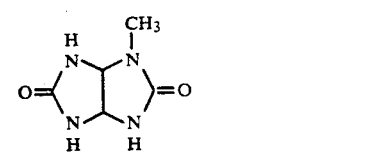
Cpd-J
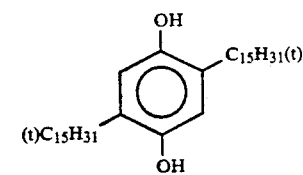
Cpd-K
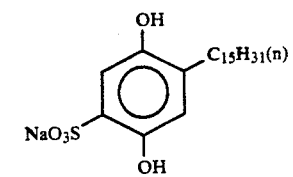
U-1
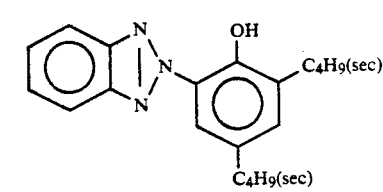

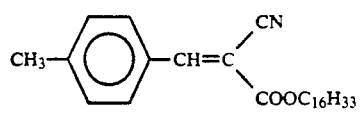 U-2
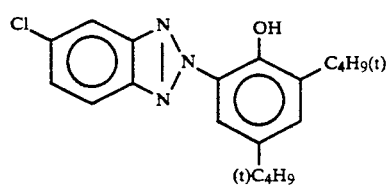 U-3
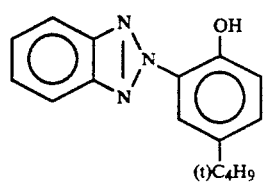 U-4
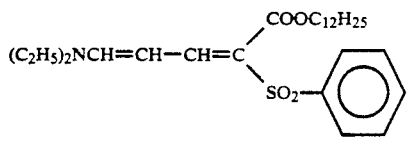 U-5
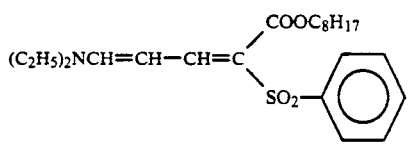 U-6
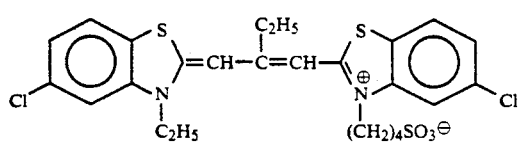 S-1
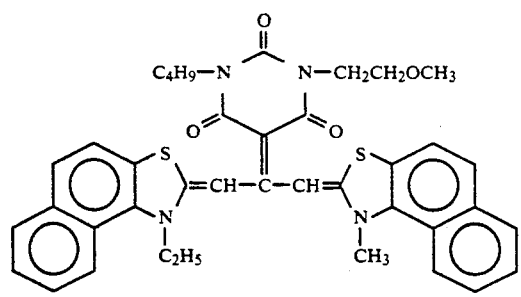 S-2
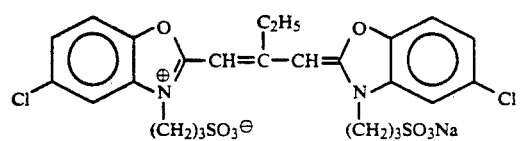 S-3
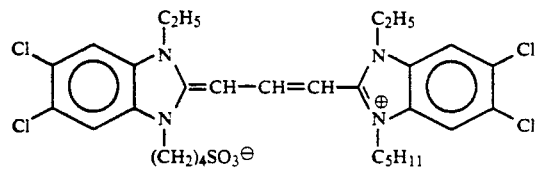 S-4

-continued
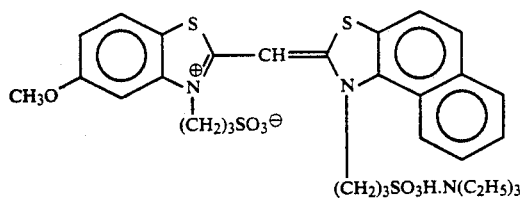 S-5
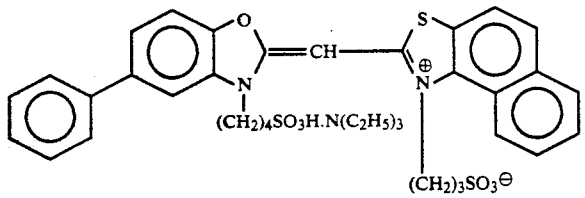 S-6
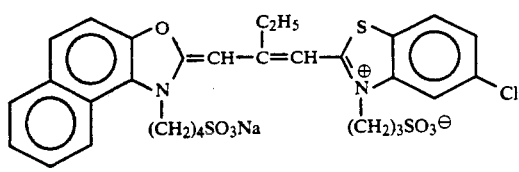 S-7
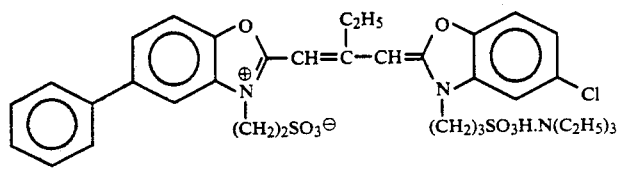 S-8
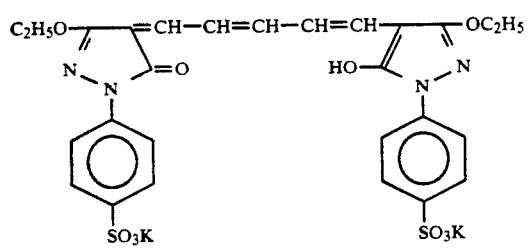 D-1
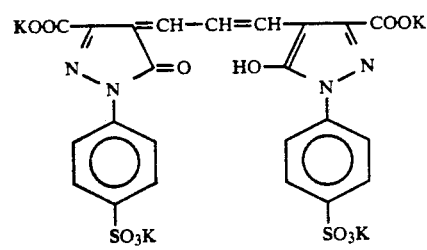 D-2
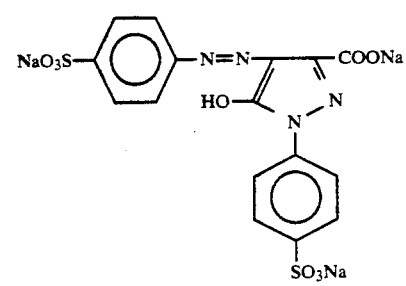 D-3

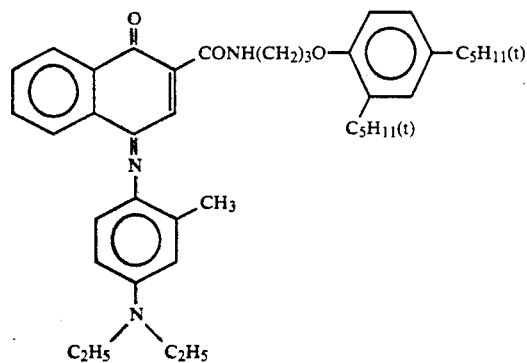 D-4
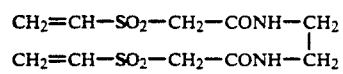 H-1
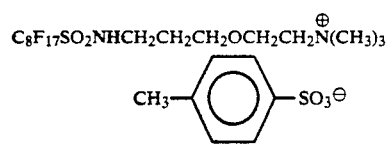 W-1
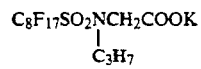 W-2
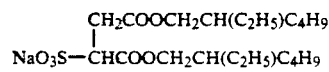 W-3
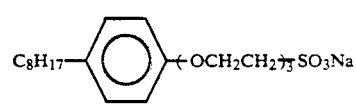 W-4
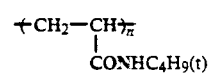 P-1
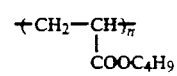 M-1
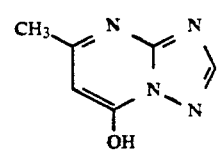 F-1
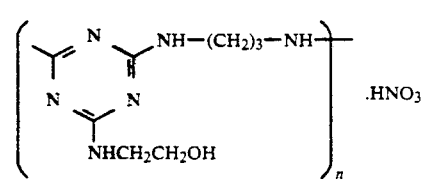 F-2
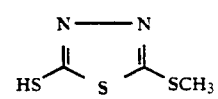 F-3

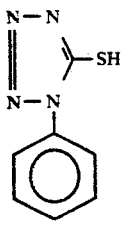 F-4

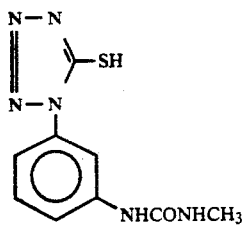 F-5

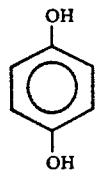 F-6

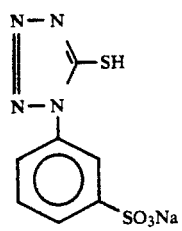 F-7

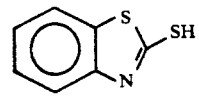 F-8

Coated samples 402 to 409 were prepared in the same manner as in the preparation of sample 401 except that an equimolar amount of each of the couplers indicated in Table 3 was used in place of each yellow coupler used in the fifteenth, sixteenth and seventeenth layers of sample 401.

These sample were exposed to blue light and subjected to the following processing stages.

| Stage | Processing Stage Time | Temp. | Tank Capacity | Replenishment Rate |
|---|---|---|---|---|
| Black-and-white development | 6 min | 38° C. | 12 l | 2.2 l/m² |
| First rinse | 2 min | 38° C. | 4 l | 7.5 l/m² |
| Reversal | 2 min | 38° C. | 4 l | 1.1 l/m² |
| Color development | 6 min | 38° C. | 12 l | 2.2 l/m² |
| Compensating | 2 min | 38° C. | 4 l | 1.1 l/m² |
| Bleaching | 6 min | 38° C. | 12 l | 0.22 l/m² |
| Fixing | 4 min | 38° C. | 8 l | 1.1 l/m² |
| Second rinse | 4 min | 38° C. | 8 l | 7.5 l/m² |
| Stabilization | 1 min | 25° C. | 2 l | 1.1 l/m² |

Each processing solution had the following composition.

| Black-and-White Developing Solution | Mother Solution | Replenisher |
|---|---|---|
| Pentasodium salt of nitrilo-N,N,N-trimethylenephosphonic acid | 2.0 g | 2.0 g |
| Sodium sulfite | 30 g | 30 g |
| Potassium hydroquinone-monosulfonate | 20 g | 20 g |
| Potassium carbonate | 33 g | 33 g |
| 1-Phenyl-4-methyl-4-hydroxymethyl-3-pyrazolidone | 2.0 g | 2.0 g |
| Potassium bromide | 2.5 g | 1.4 g |
| Potassium thiocyanate | 1.2 g | 1.2 g |
| Potassium iodide | 2.0 mg | — |
| Add water to make | 1000 ml | 1000 ml |
| pH | 9.60 | 9.60 | pH was adjusted with hydrochloric acid or potassium hydroxide.

Reversal Solution
(Replenisher being the same as mother solution)

| | |
|---|---|
| Pentasodium salt of nitrilo-N,N,N-trimethylenephosphonic acid | 3.0 g |
| Stannous chloride dihydrate | 1.0 g |
| p-Aminophenol | 0.1 g |
| Sodium hydroxide | 8 g |
| Glacial acetic acid | 15 ml |
| Add water to make | 1000 ml |
| pH | 6.0 |

-continued pH was adjusted with hydrochloric acid or sodium hydroxide.

| Color developing solution | Mother Solution | Replenisher |
|---|---|---|
| Pentasodium salt of nitrilo-N,N,N-trimethylenephosphonic acid | 2.0 g | 2.0 g |
| Sodium sulfite | 7.0 g | 7.0 g |
| Trisodium phosphate dodecahydrate | 1.0 g | — |
| Potassium bromide | 1.0 g | — |
| Potassium iodide | 90 mg | — |
| Sodium hydroxide | 3.0 g | 3.0 g |
| Citrazinic acid | 1.5 g | 1.5 g |
| N-ethyl-(β-methanesulfonamido-ethyl)-3-methyl-4-aminoaniline sulfate | 11 g | 11 g |
| 3,6-Dithia-1,8-octanediol | 1.0 g | 1.0 g |
| Add water to make | 1000 ml | 1000 ml |
| pH | 11.80 | 12.00 | pH was adjusted with hydrochloric acid or potassium hydroxide.

Compensating Solution
(Replenisher being the same as mother solution)

| | |
|---|---|
| Disodium ethylenediamine-tetraacetate dihydrate | 8.0 g |
| Sodium sulfite | 12 g |
| 1-thioglycerin | 0.4 ml |
| Sorbitan ester* | 0.1 g |
| Add water to make | 1000 ml |
| pH | 6.20 | pH was adjusted with hydrochloric acid or sodium hydroxide.

| Bleaching Solution | Mother Solution | Replenisher |
|---|---|---|
| Disodium ethylenediamine-tetraacetate dihydrate | 2.0 g | 2.0 g |
| Ethylenediaminetetraacetic acid Fe(III) ammonium dihydrate | 120 g | 120 g |
| Potassium bromide | 100 g | 100 g |
| Ammonium nitrate | 10 g | 10 g |
| Add water to make | 1000 ml | 1000 ml |
| pH | 5.70 | 5.50 | pH was adjusted with hydrochloric acid or sodium hydroxide.

Fixing Solution
(Replenisher being the same as mother solution)

| | |
|---|---|
| Ammonium thiosulfate | 8.0 g |
| Sodium sulfite | 5.0 g |
| Sodium bisulfite | 5.0 g |
| Add water to make | 1000 ml |
| pH | 6.60 | pH was adjusted with hydrochloric acid or ammonia water.

Stabilizing Solution
(Replenisher being the same as mother solution)

| | |
|---|---|
| Formalin (37%) | 5.0 ml |
| Polyoxyethylene p-monononylphenyl ether (average degree of polymerization: 10) | 5.0 ml |
| Add water to make | 1000 ml | pH was not adjusted.

Sorbitan Ester*

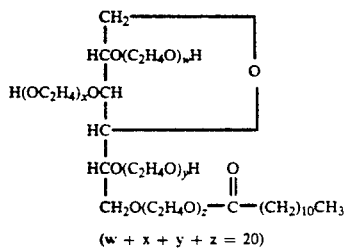

$(w + x + y + z = 20)$

The Dmax of the yellow dye image of each of the resulting samples were measured. Image preservability under the following conditions was examined. The results are shown in Table 4.

Preservability under light

This is represented by the percentage (%) of density after irradiation to initial density (1.0) after fluorescent light fading test ($1.6 \times 10^4$ lux, irradiation time: 400 hours). Preservability under dark heat:

This is represented by the percentage (%) of density after test to initial density (1.0) after standing at 80° C. and 70% RH for 7 days.

TABLE 3

| | Yellow Coupler | | |
|---|---|---|---|
| Sample No. | 15th Layer | 16th Layer | 17th Layer |
| 401 (Comp. Ex.) | C-5 | C-5, C-6 | C-6 |
| 402 (Invention) | C-5 | C-5, 24 | 24 |
| 403 (Invention) | 1 | 1, 27 | 27 |
| 404 (Invention) | 28 | 28, 25 | 25 |
| 405 (Invention) | 32 | 32, 24 | 24 |
| 406 (Invention) | 21 | 21, 21 | 21 |
| 407 (Invention) | 33 | 33, 33 | 33 |
| 408 (Invention) | 34 | 34, 34 | 34 |
| 409 (Invention) | 35 | 35, 26 | 26 |

TABLE 4

| Sample No. | Dmax | Preservability under Light | Preservability under Dark Heat |
|---|---|---|---|
| 401 (Comp. Ex.) | 2.80 | 70 | 72 |
| 402 (Invention) | 2.92 | 79 | 78 |
| 403 (Invention) | 2.98 | 83 | 78 |
| 404 (Invention) | 3.10 | 84 | 85 |
| 405 (Invention) | 3.08 | 84 | 84 |
| 406 (Invention) | 3.10 | 84 | 86 |
| 407 (Invention) | 2.94 | 78 | 76 |
| 408 (Invention) | 2.92 | 80 | 80 |
| 409 (Invention) | 3.02 | 82 | 78 |

It is clear from Table 4 that the samples 402 to of the present invention have high color density (Dmax) and have superior light preservability and superior preservability under dark heat in comparison with sample 401. Of these samples, samples 404, 405 and are particularly superior and this superiority is characteristic of monocyclic azolyl acetamide type yellow couplers.

The couplers of the present invention can form yellow dye images having high fastness to light. When the couplers represented by formula (IV) or (V) are used, the thickness of emulsion layers can be reduced so that the couplers have an effect of improving sharpness.

JP-51-104825 and JP-A-52-82423 disclose couplers whose mother solution is similar to that of a part of the couplers of the present invention. However, all examples of these couplers disclosed in the prior art are DIR couplers (restrainer-releasing couplers), and the prior art is totally different from the present invention in purpose and effect. Accordingly, the effects obtained by the present invention cannot be conceived from the disclosures of the prior art.

While the invention has been described in detail and with reference to specific embodiments thereof, it will be apparent to one skilled in the art that various changes and modifications can be made therein without departing from the spirit and scope thereof.

What is claimed is:

1. A silver halide color photographic material comprising a support having thereon at least one light sensitive silver halide emulsion layer, wherein said emulsion layer contains a coupler represented by formula (V):

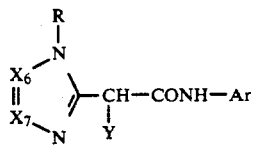

wherein:
- Y represents a group which is eliminated by coupling and has substantially no photographic effect,
- $X_6$ $X_7$ each represent a methine group or a nitrogen atom,
- R represents an alkyl group, an aryl group or a heterocyclic ring,
- Ar represents an aryl group, and
- $X_6$ and $X_7$ are not bonded to each other through their substituent groups to form a condensed ring.

2. The silver halide color photographic material as in claim 1, wherein the group represented by Y is an aryloxy group, 2,4-dioxo-1,3-imidazolidin-3-yl group, 2,4-dioxo-1,3-oxazolidin-3-yl group, 3,5-dioxo-1,2,4-triazolidin-4-yl group, 1-pyrazolyl group or 1-imidazolyl group.

3. The silver halide color photographic material as in claim 1, wherein said coupler is present in an amount of about $1 \times 10^{-6}$ to 1.0 mol per mol of silver contained in the same layer or an adjacent layer.

4. The silver halide color photographic material as in claim 1, wherein R is an alkyl group having 1 to 32 carbon atoms.

5. The silver halide color photographic material as in claim 1, wherein R is a substituted or an unsubstituted aryl group having 6 to 10 carbon atoms.

6. The silver halide color photographic material as in claim 1, wherein R is a saturated or an unsaturated substituted or unsubstituted heteroatom containing three to six-membered heterocyclic groups.

* * * * *